United States Patent
Cowen et al.

(10) Patent No.: US 12,032,660 B2
(45) Date of Patent: Jul. 9, 2024

(54) EMPATHIC ARTIFICIAL INTELLIGENCE SYSTEMS

(71) Applicant: Hume AI Inc., New York, NY (US)

(72) Inventors: Alan Cowen, New York, NY (US); Dacher Keltner, Berkeley, CA (US); Bill Schoenfeld, Tokyo (JP)

(73) Assignee: Hume AI, Inc., New York, NY (US)

( * ) Notice: Subject to any disclaimer, the term of this patent is extended or adjusted under 35 U.S.C. 154(b) by 0 days.

(21) Appl. No.: 18/322,347

(22) Filed: May 23, 2023

(65) Prior Publication Data

US 2024/0134940 A1  Apr. 25, 2024

Related U.S. Application Data

(63) Continuation of application No. 17/965,375, filed on Oct. 13, 2022, now Pat. No. 11,698,947, which is a (Continued)

(51) Int. Cl.
| | |
|---|---|
| *G06F 18/40* | (2023.01) |
| *A61B 5/16* | (2006.01) |
| *G06F 18/214* | (2023.01) |
| *G06N 20/00* | (2019.01) |
| *G16H 50/20* | (2018.01) |

(52) U.S. Cl.
CPC .............. *G06F 18/41* (2023.01); *A61B 5/165* (2013.01); *G06F 18/2148* (2023.01); *G16H 50/20* (2018.01); *G06N 20/00* (2019.01)

(58) Field of Classification Search
CPC ..... G06F 18/41; G06F 18/2148; A61B 5/165; G16H 50/20; G06N 20/00
See application file for complete search history.

(56) References Cited

U.S. PATENT DOCUMENTS

| | | |
|---|---|---|
| 10,915,798 B1 | 2/2021 | Zhang et al. |
| 2014/0315168 A1 | 10/2014 | Movellan et al. |

(Continued)

OTHER PUBLICATIONS

Cowen et al. (Dec. 18, 2020). "Semantic Space Theory: A Computational Approach to Emotion," Trends in Cognitive Sciences 25(2), 1-13.

(Continued)

*Primary Examiner* — Casey L Kretzer
(74) *Attorney, Agent, or Firm* — Morrison & Foerster LLP

(57) ABSTRACT

Embodiments of the present disclosure provide systems and methods for training a machine-learning model for predicting emotions from received media data. Methods according to the present disclosure include displaying a user interface. The user interface includes a predefined media content, a plurality of predefined emotion tags, and a user interface control for controlling a recording of the user imitating the predefined media content. Methods can further include receiving, from a user, a selection of one or more emotion tags from the plurality of predefined emotion tags, receiving the recording of the user imitating the predefined media content, storing the recording in association with the selected one or more emotion tags, and training, based on the recording, the machine-learning model configured to receive input media data and predict an emotion based on the input media data.

20 Claims, 20 Drawing Sheets

Related U.S. Application Data continuation of application No. 17/742,246, filed on May 11, 2022, now Pat. No. 11,551,031.

(60) Provisional application No. 63/209,870, filed on Jun. 11, 2021.

(56) References Cited

U.S. PATENT DOCUMENTS

| | | |
|---|---|---|
| 2017/0208362 A1 | 7/2017 | Flores et al. |
| 2018/0300851 A1 | 10/2018 | Elor et al. |
| 2019/0095775 A1 | 3/2019 | Lembersky et al. |
| 2019/0224853 A1 | 7/2019 | Gewecke et al. |
| 2020/0074154 A1* | 3/2020 | el Kaliouby ......... G06V 40/171 |
| 2020/0206631 A1 | 7/2020 | Sumant et al. |
| 2021/0133509 A1 | 5/2021 | Wall et al. |
| 2022/0398411 A1 | 12/2022 | Cowen et al. |
| 2023/0096485 A1 | 3/2023 | Cowen et al. |

OTHER PUBLICATIONS

Drimalla et al. (Apr. 6, 2021). "Imitation and recognition of facial emotions in autism: a computer vision approach," Molecular Autism 12(27); 1-15.

International Search Report and Written Opinion dated Aug. 11, 2022, directed to International Application No. PCT/US2022/72264; 19 pages.

* cited by examiner

400

Imitations of Vocal Expressions
Consent to Participate in Research

Introduction. You are being asked to participate in a research study being performed by Alan Cowen, PhD at Hume AI("the Investigator").The purpose of this consent document is to give you information about the study so that you can make an informed decision about whether to participate. Please read this document carefully. If you decide to participate in the study, you will indicate your consent to participate by checking the boxes below. Your participation in this research is voluntary.

About the Study. The purpose of this research study is to collect information about the emotions you perceive in different vocal expressions (such as laughs, gasps, or emotional speech). We hope that the data collected in this study will contribute to our understanding of human emotion. The data will also be used to help researchers and companies develop technologies such as socially aware digital assistants.

Requirements to Participate. You must be at least 18 years of age to participate in this study. You will need to have access to a computer with speakers or headphones, a microphone and a high-speed internet connection. Using your microphone, you will be recording yourself during the study, and you will need to ensure that no other person can be heard in these recordings. You will need to have a quiet, private location in which you will be able to listen to the vocal expressions and record your imitations without interruption. Finally, you will need to allow Javascript to run on this site and to disable any script blockers that are running.

Procedures. At the beginning of the study, you will be required to answer a few questions about yourself (e.g., gender, age, first language, country where from, ethnicity, zip code, and level of school completed) and to fill out a brief personality assessment.
   You will then be asked to imitate 30 vocal expressions of emotion, in a prescribed order. While you are imitating the vocal expressions, you will record yourself using a microphone interface. You will also be asked to describe the emotions conveyed by each vocal expression using the on-screen buttons and sliders. The study will take approximately 20-50 minutes to complete depending on how much effort you put in. To the extent that your imitations are convincing, you will receive a large bonus (see Compensation).

Privacy/Confidentiality. Your responses to the personality assessment and to the data linking your survey responses to your username will be password-protected, stored within an encrypted folder, and accessible only to the Investigator using end-to-end encryption. Access to your other survey responses and recordings (not including your name, username or personality assessment) will be provided to the individuals or entities and under the conditions described in Data Use and Data Sharing below.
Our Research Privacy Policy provides additional information about our personal information
handling practices.

Data Use and Data Sharing. Your data will be used by the Investigator and his affiliates to perform research and develop machine learning models. At their sole discretion, your demographics (e.g., age, gender, race, first language, national origin, education level) and task responses (recordings of yourself and ratings you submit) may also be sold to or otherwise shared with third parties, such as academic institutions and industry, corporations, and other study participants. These third parties may be anywhere in the world. You will not receive any payment other than that described in the Compensation section below. Your data may be used for additional research studies (e.g.,studies of cultural differences in emotional expression) and to develop empathic technology (e.g., developing digital assistants that respond in culturally sensitive ways). We cannot foresee all of the purposes for which your data may be used. Your data may be saved indefinitely or for the amount of time allowed by applicable law. By signing this consent document, you are giving permission for your data to be shared and used in future research studies and for educational or commercial purposes.

FIG. 4A

Note that the recordings captured using your microphone will be used in surveys and potentially other public presentations that other people see. See Audio Release below for details.

Risks of Participation. While we will take precautions to protect the information that we collect about you from unauthorized access (as described above), We cannot guarantee that these measures will be successful. As a result, there is a risk that your responses to the personality assessment, your recordings and the data linking them to your username could be compromised. If this occurs, then there is risk that data relevant to your demographics and personality could be shared with others.

Even in the absence of unauthorized access, there is a risk that your face may be recognized in the pictures shared with third parties. Thus, if you are normally uncomfortable sharing pictures of yourself, we recommend that you do not participate in this study.

Benefits of Participation. Other than the compensation described below, there are no personal benefits to participating in this research.

Compensation. You will be paid a base rate of $2.50 for completing this study. Within 1-3 days participating, you will then receive a bonus of up $5.00. The size of the bonus will depend on how people in a subsequent survey rate your vocal expressions. If the ratings are equivalent to how people rated the original vocal expressions you imitated, you will receive the maximum bonus. After that, you will not receive any other payment for participation or for the use of your data by the investigator or third parties with whom your data are shared.

Rights. Participation in research is completely voluntary. You have the right to decline to participate or to withdraw at any point in this study without penalty or loss of benefits to which you are otherwise entitled. If you choose to withdraw from the study and would like your personal information to be deleted, please let the Investigator know through the recruitment website or by email (alan@hume.ai). In that case, we may retain data that is not personal information as defined by applicable law.

Questions. If you have questions or concerns about this research or this document, or would like to amend, or make a copy of, the personal information we have about you, please contact the Investigator through the recruitment website or by email (alan@hume.ai). This project has been reviewed and approved by Heartland Institutional Review Board. Questions concerning your rights as a participant in this research may be addressed to: Heartland Institutional Review Board-Ph:866.618.HIRB-director@heartlandirb.org.

☐ I consent to participate in this study and to the Investigator collecting, storing processing, disclosing, transferring and handling my personal information for the purposes described in this Informed consent.

Audio Release

As part of this project, we will collect audio recordings of you while you participate in the research (the "Audio"). By checking the box below, you are agreeing to the terms of this Audio Release, including consenting to the following uses of the Audio.

1. The Audio can be used by the Investigator and/or his affiliates for scientific research and machine learning applications.
2. The Audio can be played to participants in other research studies.
3. The Audio can be published in scientific publications.
4. The Audio can be played at meeting of scientists.
5. The Audio can be played in classrooms to students.
6. The Audio can be played in public presentations to non-scientific groups.
7. The Audio can be played on television and radio.
8. The Audio can be used by third parties for research projects.
9. The Audio can be used by third parties and/or affiliates of the investigator for commercial applications and purposes.

In consideration for the compensation and the mutual covenants contained herein, you hereby permanently and irrevocably assign and agree to assign to Hume AI Inc. ("Hume AI") all right, title, claim, benefit and interest in and to the Audio, including all intellectual property rights thereto in perpetuity and on a royalty free and worldwide basis. To the extent that you retain any right, title or interest in or to the Audio, you hereby grant to Hume AI and its affiliates an exclusive, perpetual, irrevocable, fully paid-up, royalty-free, worldwide, sublicensable (through multiple tiers) license to, whether for commercial purposes or otherwise, reproduce, modify, distribute, display and perform (publicly and otherwise) and use the Audio, in any form or medium now known or later developed. Notwithstanding the provisions of Sections 19(4) and 30-A of the (Indian) Copyright Act, 1957, any assignment or license of the intellectual property rights made hereunder, insofar as it relates to copyright, shall not lapse nor shall the rights assigned or licensed revert to you, even if Hume AI does not exercise the rights under the assignment or license within a period of one year from the date of such assignment or license. You hereby waive any right to raise, and agree not to raise, any objection or claim before the Indian courts with respect to such assignment or license. To the extent that any such rights, title or interest in any specific work are, by operation of law, not assignable or licensable upon the terms mentioned herein above, you agree and undertaken that: (a) this will not impact your assignment or license to the rights, title and interest in all other works, (b) you will co-operate with Hume AI to enter into an arrangement that may assign or license (as the case may be) the work in question upon identical terms as contained herein however with the legal defect cured, and ⓒ you will not raise any claim against Hume AI or its licensees and/or assignees that challenges the validity of such assignment or license. You hereby also waive, to the fullest extent permitted by applicable law, any causes of action in law or equity that you may have (or may later acquire) against Hume AI or its affiliates, or their directors, officers, employees, agents, licensees, distributors or customers for copyright infringement, invasion of privacy, right of publicity or false light arising in connection with the use of the Audio. You hereby waive any right of inspection or approval of the use of the Audio, and any "moral rights" that you may have under applicable law. You confirm that you have the authority to grant the rights and releases granted in this Audio Release.

By checking the box below, you acknowledge that you have read this Audio Release, and you agree to its terms and give your consent to the uses of the Audio as indicated above.

Microworkers Username: [____]
Microworkers ID: [____]
☐ I agree to the terms above and consent to the uses of the Audio indicated above.

Personal Information

Please help us out by answering the following questions about yourself. You must answer all of the questions. If you have previously filled out *this specific form* (new to these HITs), Please scroll down and click "I filled this out in a previous hit."

What is your gender? [---Please select---∨]

How old are you? [---Please select---∨]

Which of these languages is your first language? [---Please select---∨]

What country are you from? [---Please select---∨]

What is your ethnicity (or race)? [---Please select---∨]

What is your current zip code or postal code? [Enter zipcode]

What is the highest degree or level of school you have completed? [---Please select---∨]

Think of the ladder to the right as representing the places that people occupy in society. At the top of this ladder are the people who have more money, more education and better jobs. At the bottom of the ladder are the people who have less money, less education and worse jobs(jobs with less recognition) or are unemployed. From 1 (bottom) to 10 (top), where would you place yourself on this ladder?

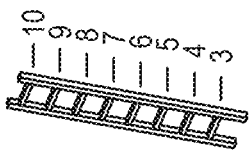

| ○1=Bottom | ○2 | ○3 | ○4 | ○5 | ○6 | ○7 | ○8 | ○9 | ○10=Top |

| Disagree strongly 1 | Disagree moderately 2 | Disagree a little 3 | Neither agree nor disagree 4 | Agree a little 5 | Agree moderately 6 | Agree strongly 7 |

FIG. 7A

I often feel nervous and restless.
○1 ○2 ○3 ○4 ○5 ○6 ○7

In most ways my life is close to my ideal.
○1 ○2 ○3 ○4 ○5 ○6 ○7

I'll say anything to get what I want.
○1 ○2 ○3 ○4 ○5 ○6 ○7

I could easily write a lot of synonyms for emotion words like happiness or sadness.
○1 ○2 ○3 ○4 ○5 ○6 ○7

I like to use clever manipulation to get my way.
○1 ○2 ○3 ○4 ○5 ○6 ○7

I tend to make decisions easily.
○1 ○2 ○3 ○4 ○5 ○6 ○7

I have a rich vocabulary to describe my emotions.
○1 ○2 ○3 ○4 ○5 ○6 ○7

It's wise to avoid direct conflict with others because they may be useful in the future.
○1 ○2 ○3 ○4 ○5 ○6 ○7

I like to get acquainted with important people.
○1 ○2 ○3 ○4 ○5 ○6 ○7

So far I have gotten the important things I want in life.
○1 ○2 ○3 ○4 ○5 ○6 ○7

I feel embarrassed if someone compliments me.
○1 ○2 ○3 ○4 ○5 ○6 ○7

People who mess with me always regret it.
○1 ○2 ○3 ○4 ○5 ○6 ○7

I see myself as:

...Extraverted, enthusiastic.
○1 ○2 ○3 ○4 ○5 ○6 ○7

...Critical, quarrelsome.
○1 ○2 ○3 ○4 ○5 ○6 ○7

...Dependable, self-disciplined.
○1 ○2 ○3 ○4 ○5 ○6 ○7

...Anxious, easily upset.
○1 ○2 ○3 ○4 ○5 ○6 ○7

...Open to new experiences, complex.
○1 ○2 ○3 ○4 ○5 ○6 ○7

...Reserved, quiet.
○1 ○2 ○3 ○4 ○5 ○6 ○7

...Sympathetic, warm.
○1 ○2 ○3 ○4 ○5 ○6 ○7

...Disorganized, careless.
○1 ○2 ○3 ○4 ○5 ○6 ○7

...Calm, emotionally stable.
○1 ○2 ○3 ○4 ○5 ○6 ○7

...Conventional, uncreative.
○1 ○2 ○3 ○4 ○5 ○6 ○7

[ I filled this out in a previous hit. ]

801
- Use the "Click and Hold to Record" button to record your best imitation of the expression.
- Remember, you will receive bonuses of up to $5.00 ($.17/expression) if your imitations are rated similarly to the originals.
- Describe the emotions conveyed by the original voice using the buttons below.
- Rate the intensity of each emotion on a 1-100 scale. There is no need to be exact.
- If you choose randomly, you may be rejected.
- After you have selected at least one emotion, click to continue to the next expression.

803 ▷ 0:00 / 0:00 🔊

Record yourself imitating the same emotional expression *in your own voice* (you don't need to mimic the person's voice). Repeat until you are satisfied that you have captured the emotion conveyed. You can select a previous recording if needed.

807 What emotions is this person feeling? Select all that apply.

| Admiration | Adoration | Aesthetic appreciation | Amusement |
| Anger | Anxiety | Awe | Awkwardness | Boredom | Calmness |
| Concentration | Contemplation | Confusion | Contempt |
| Contentment | Craving | Determination | Disappointment |
| Disgust | Distress | Doubt | Ecstasy | Embarrassment |
| Empathic pain | Entrancement | Envy | Excitement | Fear |
| Horror | Interest | Joy | Love | Nostalgia | Pain | Pride |
| Satisfaction | Sexual desire | Shame | Surprise (negative) |
| Triumph |
| Realization | Relief | Romance | Sadness |
| Surprise (positive) | Sympathy | Tiredness |

Continue

805 Click and Hold to Record
Click and drag to reposition

901
- Use the "Click and Hold to Record" button to record your best imitation of the expression.
- Remember, you will receive bonuses of up to $5.00 ($.17/expression) if your imitations are rated similarly to the originals.
- Describe the emotions conveyed by the original voice using the buttons below.
- Rate the intensity of each emotion on a 1-100 scale. There is no need to be exact.
- If you choose randomly, you may be rejected.
- After you have selected at least one emotion, click to continue to the next expression.

907

Record yourself imitating the same emotional expression *in your own voice* (you don't need to mimic the person's voice). Repeat until you are satisfied that you have captured the emotion conveyed. You can select a previous recording if needed.

903 △ 0:00 / 0:00 🔊

What emotions is this person feeling? Select all that apply.

| Admiration | Adoration | Aesthetic appreciation | Amusement |
| Anger | Anxiety | Awe | Awkwardness | Boredom | Calmness |
| Concentration | Contemplation | Confusion | Contempt |
| Contentment | Craving | Determination | Ecstasy | Disappointment |
| Disgust | Distress | Entrancement | Envy | Embarrassment |
| Empathic pain | Interest | Joy | Love | Excitement | Fear |
| Horror | Sexual desire | Shame | Nostalgia | Pride |
| Satisfaction | | | | Pain | Surprise (negative) |
| Triumph |
| Realization | Relief | Romance |
| Surprise (positive) | Sadness | Sympathy | Tiredness |

905
Click and Hold to Record
Click and drag to reposition

909 △ 0:00 🔊

911
Distress intensity: ○────── 0
Nostalgia intensity: ○────── 0

○ Use the "Capture" button to photograph your best imitation of the expression.
○ Remember, you will receive bonuses of up to $5.00 ($.17/expression) if your imitations are rated similarly to the originals.
○ Describe the emotions conveyed by the face using the buttons below.
○ Rate the intensity of each emotion on a 1-100 scale. There is no need to be exact.
○ If you choose randomly, you may be rejected.
○ After you have selected at least one emotion, click to continue to the next expression.

Click and drag to reposition

Capture

What emotions is this person feeling? Select all that apply.

| Admiration | Adoration | Aesthetic appreciation | Amusement | Anger | Anxiety | Awe | Awkwardness |
| Boredom | Calmness | Concentration | Contemplation | Confusion | Contempt | Contentment | |
| Craving | Determination | Disappointment | Disgust | Distress | Doubt | Ecstasy | Embarrassment |
| Empathic pain | Entrancement | Envy | Excitement | Fear | Guilt | Horror | Interest | Joy | Love |
| Nostalgia | Pain | Pride | Realization | Relief | Romance | Sadness | Satisfaction | Sexual desire |
| Shame | Surprise (negative) | Surprise (positive) | Sympathy | Tiredness | Triumph |

Thank you very much for participating in this study.

Please enter any comments you have about this study in the box below, then click "Submit".

[ Submit ]

1200 ⟶

Thank you! Your completion code is 1 cfbdq.

FIG. 15A

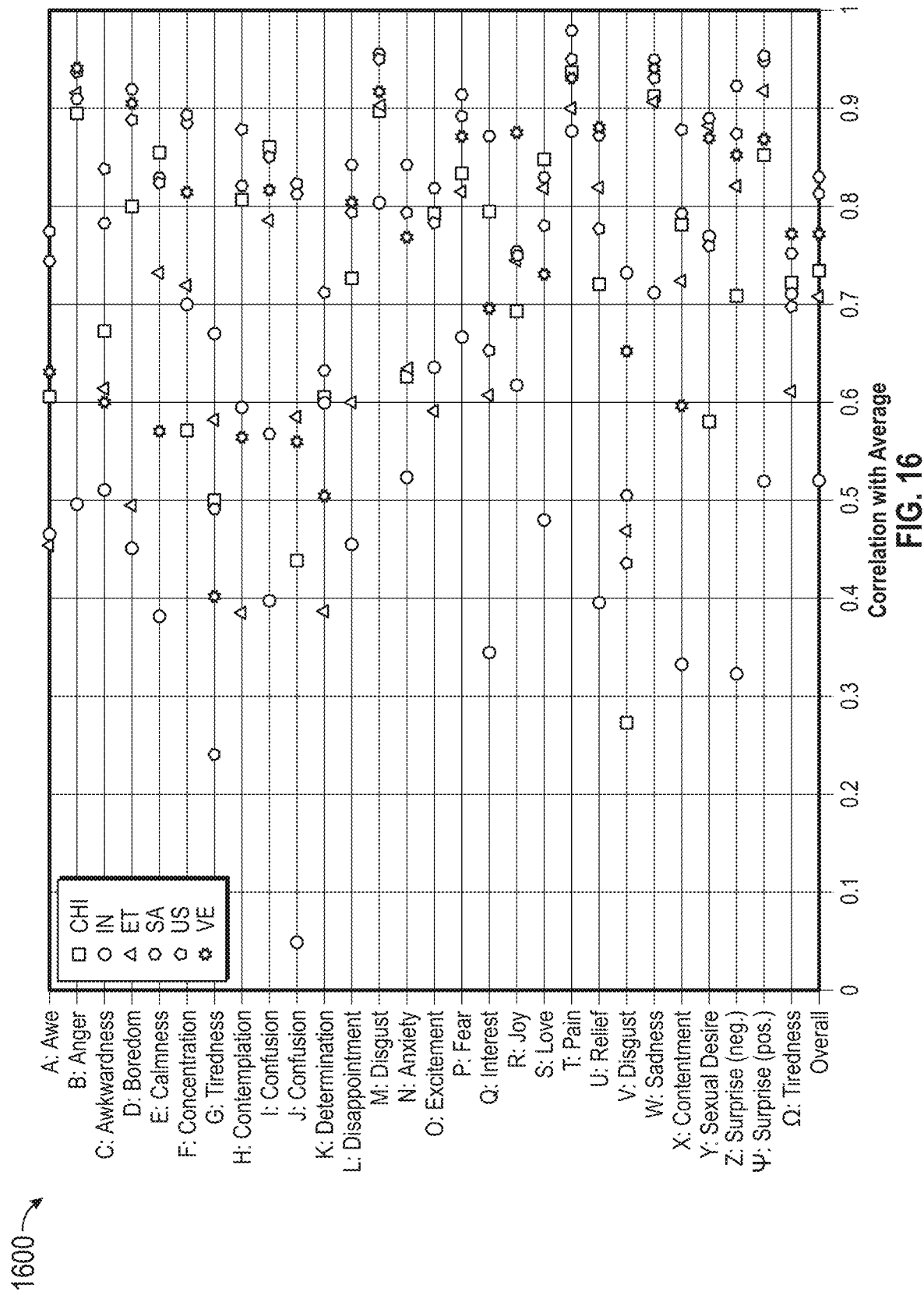

EMPATHIC ARTIFICIAL INTELLIGENCE SYSTEMS

CROSS-REFERENCE TO RELATED APPLICATIONS

This application is a continuation of U.S. application Ser. No. 17/965,375, filed Oct. 13, 2022, which is a continuation of U.S. application Ser. No. 17/742,246, filed May 11, 2022, which claims priority to and the benefit of U.S. Provisional Patent Application No. 63/209,870, filed Jun. 11, 2021, the disclosure of which are herein incorporated by reference in their entirety.

FIELD OF THE DISCLOSURE

The present disclosure relates generally to machine-learning models and techniques, and more specifically to obtaining data for training machine-learning models to identify emotional facial expressions.

BACKGROUND OF THE DISCLOSURE

Current artificial intelligence ("AI") systems for the measurement of emotional expression ("empathic AI algorithms") capture only a fraction of the information that is intentionally or unintentionally conveyed by emotional expressions to perceivers. The main bottleneck in training better empathic AI algorithms (e.g., machine-learning algorithms that predict participant emotion-related behavioral responses, including ratings and recorded responses, from media data) is the quality and quantity of training data. Due to data limitations, empathic AI algorithms currently (1) fail to recognize many dimensions of emotional expression, as a result of limitations in the scope and diversity of the training data and (2) suffer from perceptual biases, as a result of confounding variables in the training data.

BRIEF SUMMARY OF THE DISCLOSURE

Embodiments of the present disclosure provide systems and methods for obtaining training data to train machine-learning models to accurately predict emotion across a wide variety of subjects. For example, methods according to the present disclosure are directed to collecting training data for empathic AI overcomes the challenges described above by using experimental manipulation to collect data that represents a richer, more balanced, and more diverse set of expressions; avoiding perceptual biases and confounds by gauging participants' own representations, beliefs, and/or ratings of the meanings of their expressions; and further avoiding perceptual biases and confounds by systematically collecting recordings of a balanced set of emotional expressions from different demographic or cultural groups Embodiments in accordance with the present disclosure include systems, methods, and techniques for creating a system for predicting emotions from received media data. Methods in accordance with the present disclosure include: displaying a user interface comprising: a predefined media content, a plurality of predefined emotion tags, and a user interface control for controlling a recording of the user imitating the predefined media content (e.g., a recording user interface control). The methods further include receiving, from a user, a selection of one or more emotion tags from the plurality of predefined emotion tags. The methods further include receiving a recording of the user imitating the predefined media content. The methods further include storing the recording in association with the selected one or more emotion tags. The methods further include training, based on the recording, a machine-learning model configured to receive input media data and predict an emotion based on the input media data.

In one or more embodiments of the present disclosure, displaying the user interface further comprises displaying a user interface control for providing a playback of the predefined media content.

In one or more embodiments of the present disclosure, the methods further include displaying a preview of the recording on the user interface. In one or more embodiments of the present disclosure, the preview of the recording is displayed side-by-side with the predefined media content. In one or more embodiments of the present disclosure, the preview of the recording comprises a preview recording control for providing a playback of the recording.

In one or more embodiments of the present disclosure, the methods further include: inputting data corresponding to a plurality of demographic groups into the trained machine-learning model to generate a plurality of outputs and identifying a bias of the trained machine-learning model based on the plurality of outputs.

In one or more embodiments of the present disclosure, the methods further include: receiving one or more inputs indicative of one or more characteristics of the user, storing the recording in association with the one or more characteristics of the user, selecting the recording based on the associated one or more characteristics of the user, and training the machine-learning model based on the recording. In one or more embodiments of the present disclosure, the methods further include displaying a prompt for the one or more characteristics of the user. In one or more embodiments of the present disclosure, the one or more characteristics include one or more selected from a gender, an age, one or more races or ethnicities, a country of origin, a first language, a second language, personality, well-being, mental health, or a subjective socioeconomic status. In one or more embodiments of the present disclosure, the methods further include selecting the media content used to train the machine-learning model based on the one or more characteristics of the user.

In one or more embodiments of the present disclosure, the predefined media content includes one or more of text data, audio, video, or image. In one or more embodiments of the present disclosure, the input media data includes one or more of text data, audio data, video data, or image data. In one or more embodiments of the plurality of predefined emotion tags comprise one or more of admiration, adoration, aesthetic appreciation, amusement, anger, annoyance, anxiety, approval, awe, awkwardness, boredom, calmness, compulsion, concentration, confusion, connectedness, contemplation, contempt, contentment, craving, curiosity, delusion, depression, determination, disappointment, disapproval, disgust, disorientation, distaste, distress, dizziness, doubt, dread, ecstasy, elation, embarrassment, empathetic pain, entrancement, envy, excitement, fear, frustration, gratitude, grief, guilt, happiness, hopelessness, horror, humor, interest, intimacy, irritability, joy, love, mania, melancholy, mystery, nostalgia, obsession, pain, panic, pride, realization, relief, romance, sadness, sarcasm, satisfaction, self-worth, serenity, seriousness, sexual desire, shame, spirituality, surprise (negative), surprise (positive), sympathy, tension, tiredness, trauma, triumph, warmth, and wonder.

In one or more embodiments of the present disclosure, the user is a first user, and the method further comprises: receiving a second user's selection of one or more emotion tags from the plurality of emotion tags; and comparing the first user's selection and the second user's selection; and determining a compensation for the user. In such embodiments, the method further comprises determining whether to train the machine-learning model using the recording based on the comparison. In such embodiments, the method further comprises receiving a second recording imitating the media content from the second user.

In one or more embodiments of the present disclosure, the method further comprises receiving a user input indicative of an intensity level corresponding to each of the selected emotion tags. In one or more embodiments of the present disclosure, the machine-learning model is one selected from a supervised model, an unsupervised model, and a self-supervised model.

Embodiments of the present disclosure further comprise a method for creating a system for generating a media output from an input indicative of an emotion. This method comprises providing a user interface comprising: a predefined media content, a plurality of predefined emotion tags, and a recording user interface control. The method further comprises receiving, from a user, a selection of one or more emotion tags from the plurality of predefined emotion tags. The method further comprises receiving a recording of the user imitating the media content. The method further comprises storing the recording in association with the selected one or more emotion tags. The method further comprises training, based on the recording, a machine-learning model configured to receive an input indicative of an emotion and generate a media output comprising a vocal expression or a facial expression of the emotion.

In one or more embodiments of the present disclosure, media output is speech data. In one or more embodiments of the present disclosure, the media output is image data. In one or more embodiments of the present disclosure, displaying the user interface further comprises displaying a user interface control for providing a playback of the predefined media content.

In one or more embodiments of the present disclosure, the method for creating a system for generating a media output from an input indicative of an emotion further comprises displaying a preview of the recording on the user interface. In such embodiments, the preview of the recording is displayed side-by-side with the predefined media content. In one or more embodiments of the present disclosure, the preview of the recording comprises a preview recording control for providing a playback of the recording.

In one or more embodiments of the present disclosure, the method for creating a system for generating a media output from an input indicative of an emotion further comprises inputting data corresponding to a plurality of demographic groups into the trained machine-learning model to generate a plurality of outputs and identifying a bias of the trained machine-learning model based on the plurality of outputs.

In one or more embodiments of the present disclosure, the method for creating a system for generating a media output from an input indicative of an emotion further comprises receiving one or more inputs indicative of one or more characteristics of the user, storing the recording in association with the one or more characteristics of the user, selecting the recording based on the associated one or more characteristics of the user, and training the machine-learning model based on the recording. In such embodiments, the method can further comprise displaying a prompt for the one or more characteristics of the user. In such embodiments, the one or more characteristics include one or more selected from a gender, an age, one or more races or ethnicities, a country of origin, a first language, a second language, personality, well-being, mental health, or a subjective socio-economic status. In one or more embodiments, of the present disclosure, the method can further comprise selecting the media content used to train the machine-learning model based on the one or more characteristics of the user.

In one or more embodiments of the present disclosure, the predefined media content includes one or more of text data, audio, video, or image. In one or more embodiments of the present disclosure, the input media data includes one or more of text data, audio data, video data, or image data. In one or more embodiments of the present disclosure, the plurality of predefined emotion tags comprise one or more of admiration, adoration, aesthetic appreciation, amusement, anger, annoyance, anxiety, approval, awe, awkwardness, boredom, calmness, compulsion, concentration, confusion, connectedness, contemplation, contempt, contentment, craving, curiosity, delusion, depression, determination, disappointment, disapproval, disgust, disorientation, distaste, distress, dizziness, doubt, dread, ecstasy, elation, embarrassment, empathetic pain, entrancement, envy, excitement, fear, frustration, gratitude, grief, guilt, happiness, hopelessness, horror, humor, interest, intimacy, irritability, joy, love, mania, melancholy, mystery, nostalgia, obsession, pain, panic, pride, realization, relief, romance, sadness, sarcasm, satisfaction, self-worth, serenity, seriousness, sexual desire, shame, spirituality, surprise (negative), surprise (positive), sympathy, tension, tiredness, trauma, triumph, warmth, and wonder.

In one or more embodiments of the present disclosure, the user is a first user, the and the method further comprises receiving a second user's selection of one or more emotion tags from the plurality of emotion tags and comparing the first user's selection and the second user's selection; and determining a compensation for the user. In such embodiments the method can further comprise determining whether to train the machine-learning model using the recording based on the comparison. The method can further comprise receiving a second recording imitating the media content from the second user.

In one or more embodiments of the present disclosure, the method for creating a system for generating a media output from an input indicative of an emotion further comprises receiving a user input indicative of an intensity level corresponding to each of the selected emotion tags. In one or more embodiments of the present disclosure, the machine-learning model is one selected from a supervised model, an unsupervised model, and a self-supervised model.

Embodiments of the present disclosure further comprise a user interface for creating a system for predicting emotions of a received video. The user interface can comprise: a predefined media content, a plurality of predefined emotion tags, and a recording user interface control. The user interface can be configured to: receive, from a user, a selection of one or more emotion tags from the plurality of predefined emotion tags and receive a recording of the user imitating the predefined media content. The recording can be used to train a machine-learning model configured to receive input media data and predict an emotion based on the input media data.

Embodiments of the present disclosure provide a user interface further comprising a control for providing a playback of the predefined media content. Embodiments of the present disclosure provide a user interface further comprising a preview of the recording on the user interface. In such embodiments, the preview of the recording is displayed side-by-side with the predefined media content. Further, in such embodiments, the preview of the recording comprises a preview recording control for providing a playback of the recording.

Embodiments of the present disclosure further comprise methods for predicting emotion in a media data. The methods comprise receiving the media data. The methods further comprise inputting the media data as an input to a machine-learning model trained by a process comprising: displaying a user interface; receiving, from a user, a selection of one or more emotion tags from the plurality of predefined emotion tags; receiving a recording of the user imitating the predefined media content; storing the recording in association with the selected one or more emotion tags; and training, based on the recording, the machine-learning model. In such embodiments, the user interface can comprise a predefined media content, a plurality of predefined emotion tags, and a recording user interface control.

In one or more embodiments of the present disclosure, the method for predicting emotion in a media data can further comprise obtaining from the trained machine-learning model an emotion prediction and using the emotion prediction to create a diagnosis based on the emotion prediction. In such embodiments, the method can further comprise obtaining from the trained machine-learning model an emotion prediction; and interpreting a user utterance based on the emotion prediction. In one or more embodiments, the method can further comprise obtaining from the trained machine-learning model an emotion prediction, and generating an emotional expression on a virtual character in a virtual reality environment based on the emotion prediction. In one or more embodiments, the method can further comprise obtaining from the trained machine-learning model an emotion prediction; and altering a virtual reality environment based on the emotion prediction. In one or more embodiments, the method can further comprise obtaining from the trained machine-learning model an emotion prediction, and providing feedback of the media item based on the emotion prediction. In one or more embodiments, the method can further comprise obtaining from the trained machine-learning model an emotion prediction, obtaining media content based on the emotion prediction, and operating a virtual assistant based on the obtained media content. In one or more embodiments, the method can further comprise obtaining from the trained machine-learning model an emotion prediction, obtaining media content based on the emotion prediction, and modifying a virtual reality environment based on the media content.

BRIEF DESCRIPTION OF THE FIGURES

FIGS. 4A and 4B illustrate an exemplary consent form, in accordance with some embodiments of this disclosure.

FIG. 5 illustrates an exemplary consent form, in accordance with some embodiments of this disclosure.

FIGS. 7A and 7B illustrate an exemplary questionnaire, in accordance with some embodiments of this disclosure.

FIG. 8 illustrates an exemplary user interface, in accordance with some embodiments of this disclosure.

FIG. 9 illustrates an exemplary user interface, in accordance with some embodiments of this disclosure.

FIG. 10 illustrates an exemplary user interface, in accordance with some embodiments of this disclosure.

FIG. 15A illustrates an exemplary plot that shows a distributions of emotion ratings, in accordance with some embodiments of this disclosure.

FIG. 16 illustrates an exemplary plot that shows the loading correlations across countries and dimensions of facial expression, in accordance with some embodiments of this disclosure.

DETAILED DESCRIPTION OF THE DISCLOSURE

Figure 1:
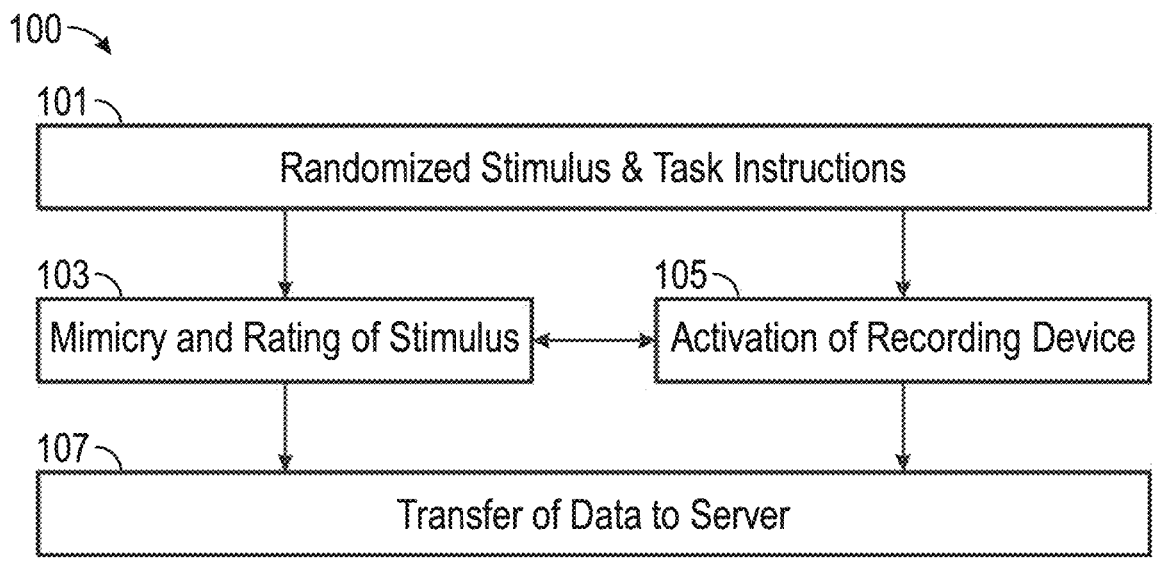
FIG. 1 illustrates an exemplary process for obtaining training data for machine-learning algorithms, according to embodiments of this disclosure.

Current artificial intelligence ("AI") systems for the measurement of emotional expression ("empathic AI algorithms") capture only a fraction of the information that is intentionally or unintentionally conveyed by emotional expressions to perceivers. One of the challenges to training better empathic AI algorithms (e.g., machine-learning algorithms that predict participant emotion-related behavioral responses) is the quality and quantity of training data. Due to data limitations, empathic AI algorithms currently fail to recognize many dimensions of emotional expression and suffer from perceptual biases.

For example, conventional AI systems for measuring emotional expressions are limited by the scope and generalizability of the training data. In images drawn from public sources, expressions such as the neutral face or posed smile are dramatically overrepresented, while expressions of genuine fear, anger, and many other emotions are very sparse. In datasets drawn from academia, the focus is generally on posed stereotypical facial expressions of six emotions (anger, disgust fear, happiness, sadness, and surprise), which represent only a tiny fraction of the emotional expressions found in everyday life. Consequently, machine-learning algorithms (e.g., empathic ML/AI algorithms) trained on these data do not generalize well to most real-life samples.

Additionally, conventional AI systems for measuring emotional expressions are limited by perceptual biases in training data. Empathic AI algorithms inherit perceptual biases from training data. For instance, in ratings of images drawn from public sources, people with sunglasses are typically perceived as expressing pride and labeled (sometimes incorrectly) as expressing pride. As a result, algorithms trained on perceptual ratings of natural images may label people wearing sunglasses as expressing pride. Moreover, algorithms are biased by demographic imbalances in the expression of specific emotions within public sources of data. For example, young men are more often found expressing triumph than women or older individuals, due to the disproportionate representation of young men playing sports. By contrast, academic datasets attempt to represent people of different demographics expressing the same emotions, but as noted above these datasets are generally very small and focus on a narrow range of emotional expressions.

The method described here for collecting training data for empathic AI overcomes these challenges by using experimental manipulation to collect data that represents a richer, more balanced, and more diverse set of expressions, avoiding perceptual biases and confounds by gauging participants' own representations, beliefs, and/or ratings of the meanings of their expressions, and further avoiding perceptual biases and confounds by systematically collecting recordings of a balanced set of emotional expressions from different demographic or cultural groups.

Embodiments of the present disclosure include a number of technical advantages conferred by obtaining improved training data. For example, embodiments of the present disclosure include techniques for obtaining training data that are simultaneously: ecologically valid, large scale, emotionally rich, demographically diverse, experimentally controlled, collected from fully consenting participants, and psychologically informative. For example, embodiments of the present disclosure can collect ecologically valid data that represents everyday behavior of individuals. As another example, embodiments of the present disclosure can collect large-scale data that comprises hundreds of thousands of samples. As another example, embodiments of the present disclosure can collect emotionally rich data capturing a sufficiently diverse and statistically balanced set of behaviors. As another example, embodiments of the present disclosure can collect demographically diverse data representing different groups and cultures. As another example, embodiments of the present disclosure can collect experimentally controlled data in such a way that it is possible to account for the effects of potentially confounding variables. As another example, embodiments of the present disclosure can collect this data from participants who have fully consented to the use of the data for training AI algorithms, via a consent process that complies with local data protection laws. As another example, embodiments of the present disclosure can collect psychologically informative data that includes participants' own ratings of their behavior.

By using improved training data, the machine-learning models can be trained with less training data and would require less input data, thus improving memory usage and management. Further, such models can require less processing power for training and for performing the trained tasks. Thus, embodiments of the present disclosure can improve the functioning of a computer system by improving processing speed, lowering power consumption, and allowing for efficient use of computer memory and processing power.

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown, but are to be accorded the scope consistent with the claims.

Although the following description uses terms "first," "second," etc. to describe various elements, these elements should not be limited by the terms. These terms are only used to distinguish one element from another. For example, a first graphical representation could be termed a second graphical representation, and, similarly, a second graphical representation could be termed a first graphical representation, without departing from the scope of the various described embodiments. The first graphical representation and the second graphical representation are both graphical representations, but they are not the same graphical representation.

The terminology used in the description of the various described embodiments herein is for the purpose of describing particular embodiments only and is not intended to be limiting. As used in the description of the various described embodiments and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

The term "if" is, optionally, construed to mean "when" or "upon" or "in response to determining" or "in response to detecting," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]," depending on the context.

FIG. 1 illustrates an exemplary process 100 for obtaining training data for machine-learning algorithms according to embodiments of this disclosure. Process 100 is performed, for example, using one or more electronic devices implementing a software platform. In some examples, process 100 is performed using a client-server system, and the blocks of process 100 are divided up in any manner between the server and a client device. In other examples, the blocks of process 100 are divided up between the server and multiple client devices. In other examples, process 100 is performed using only a client device or only multiple client devices. In process 100, some blocks are, optionally, combined, the order of some blocks is, optionally, changed, and some blocks are, optionally, omitted. In some examples, additional steps may be performed in combination with the process 100. Accordingly, the operations as illustrated (and described in greater detail below) are exemplary by nature and, as such, should not be viewed as limiting.

At Block 101, an exemplary system (e.g., an application executed on one or more electronic devices) can obtain an experimental stimulus and/or task from a database of stimuli and/or tasks and present the experimental stimulus to a participant. In one or more examples, the task may be randomly selected form the database. The system can then, prompt the participant to behave in a manner that depends on how they perceive or make sense of the stimulus or task. In some embodiments, the stimulus may include a textual description of the emotion to be acted out rather than media data, e.g., a photo or video. For example, participants may be asked to behave based on a textual instruction (e.g., "produce a facial expression that shows surprise").

In one or more examples, the participant may be reminded that their compensation will depend on a comparison between ratings or measures behavior and ratings or measures of the stimulus. In this manner the system can provide a motivation to the participant to provide an accurate response to the prompt.

At Block 103, the exemplary system can receive a mimicry response and rating of the experimental stimulus from the user. In some embodiments, the system can receive a participant response upon receiving an indication that the participant is ready, e.g., the system can receive the participant response while or after receiving an indication that the participant pressed a button.

In one or more examples, before or after receiving the behavioral response recorded by the participant using the recording devices (e.g., webcam and/or microphone), the system can receive a rating of the experimental stimulus from the participant. In one or more examples, the system can present the user with buttons, sliders, text input, and/or other forms of input such as a free response (e.g. a textual response describing the stimulus), for the participant provide a response corresponding to a rating of the experimental stimulus. In some embodiments, the system may not present a ratings survey to the participant to enable the participant to rate the stimulus.

In some embodiments, the system can perform validation of the recorded behavioral response of the user. In some embodiments, the validation can be based upon one or more predefined thresholds. For instance, if a predetermined parameter (e.g., file size, duration, and/or signal intensity) of the recording is not within a predefined threshold, the system can indicate that the recording is not accepted. In some embodiments, a user may not proceed with the data collection process if the recording is not validated.

In some embodiments, the validation can be performed based on other participants' ratings. For instance, a participant's recorded behavioral responses may be used as stimuli in surveys responded to by other participants. The other participants' responses may be used to validate the original recordings for use as machine-learning training data as well as to determine the original participants' compensation.

As an example, the system can present a first stimulus to a first participant, receive a selection of a first set of emotion tags and corresponding emotion intensities associated with the first stimulus, and capture a first recording by the first participant mimicking the first stimulus. The first recording of the first participant may later be presented as a second stimulus to a second participant. Accordingly, the system can present the second stimulus to the second participant and receive a selection of a second set of emotion tags and corresponding emotion intensities associated with the second stimulus. If the second set of emotion tags and intensities associated with the first recording/second stimulus are identical or similar to the first set of emotion tags and intensities associated with the first stimulus, the first recording may be validated. Measures of similarity for purpose of validating the first recording may include a percentage overlap in emotion tags, the correlation (such as the Pearson product-moment correlation coefficient) between emotion intensities associated the first recording and those associated with the first stimulus, or the inverse of the distance (such as Euclidean distance) between emotion intensities associated the first recording and those associated with the first stimulus.

At Block 105, the system can activate the recording device located on a participant's computer or personal device. In some embodiments, the recording device can be either activated immediately upon the execution of the experimental trial or activated through a button that the participant is told to press when ready to begin their response. The recording device may either continuously record during the full duration of the trial, record only one image or for a fixed duration of time, or record until some event occurs, such as the cessation of a video stimulus. As discussed above with respect to Block 103, the recording may capture a mimicry response of the participant to an experimental stimulus.

At Block 107, the system can transfer the recorded data and survey data to a server. In some embodiments, participants recorded behaviors, metadata such as current time and the filename of the stimulus, and/or ratings of the stimulus can be transferred through the Internet to a data storage server.

Figure 2:
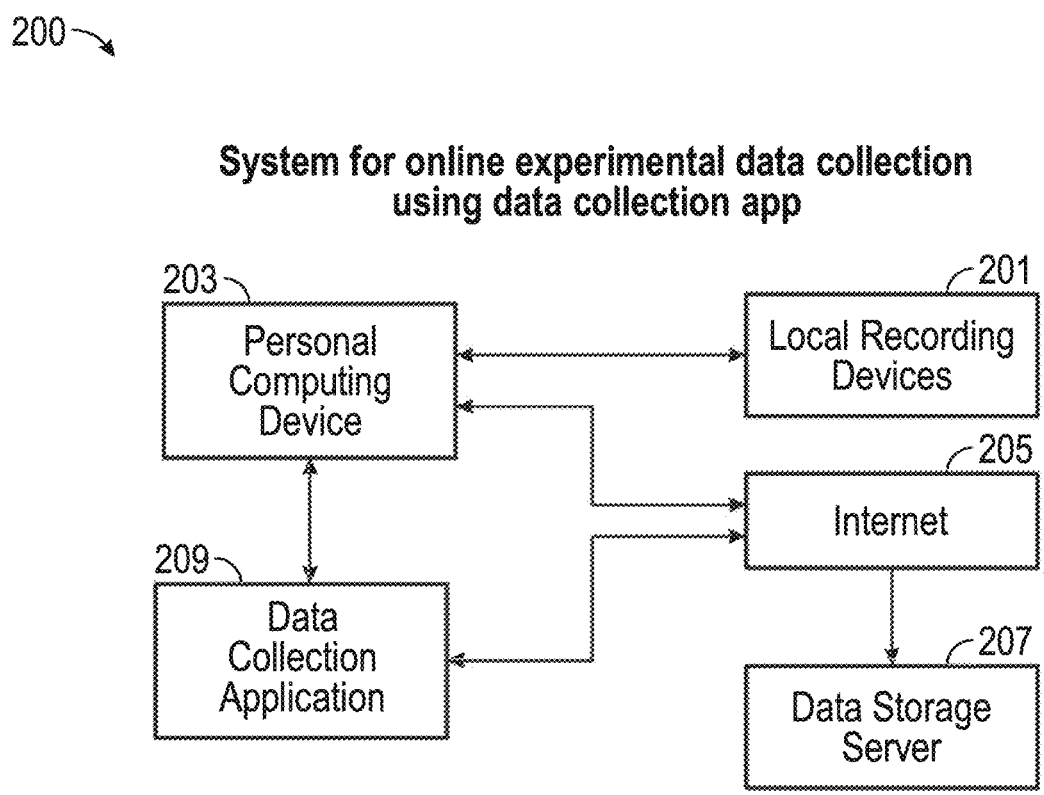
FIG. 2 illustrates an exemplary system for online experimental data collection, in accordance with some embodiments of this disclosure.

FIG. 2 illustrates an exemplary system 200 for obtaining training data for machine-learning algorithms according to embodiments of this disclosure. The exemplary system can include a personal computing device 203, a local recording device 201, a data collection application 209, the internet 205, and a data storage server 207. In one or more examples, the exemplary system for obtaining training data for machine-learning algorithms can optionally, omit and/or combine one or more of these elements.

In some embodiments, the personal computing device 203 can correspond to the device through which a participant accesses the data collection application 209 via the Internet 205. In one or more examples, the personal computing device 203 can include, but is not limited to a laptop or a smartphone.

In some embodiments, the personal computing device 203 can be equipped with or connected to local recordings devices 201. In one or more examples, the local recordings devices 201 can include, but are not limited to webcams, and/or microphones, that are accessed by the data collection application 209.

In some embodiments, the data collection application 209, can be in the form of a website, web application, desktop application, or mobile application. In one or more examples, the data collection application 209 can present participants with instructions, consent processes, and experimental trials. In one or more examples, the data collection application 209 can collect data based on participants' responses, e.g., participant's mimicry responses and survey responses.

In some embodiments, the data collected using the data collection application 209 can be transferred via the Internet 205 to a data storage server 207. The data may be stored in a file server or database with associations between participants' self-reported demographic and personality data, recordings (media files), metadata, and labels. Self-reported demographic and personality data may include gender, age, race/ethnicity, country of origin, first and/or second language, and answers to psychological survey questions that indicate personality, well-being, mental health, and/or subjective socioeconomic status. Recordings may include images, audio, or video of participants' behaviors in response to experimental stimuli and/or tasks. Metadata may include the participant identifier, upload time, survey identifier, stimulus filename and/or task description, country/ location in which data collection application was accessed, experimental trial number, and/or trial duration. Labels may include emotions selected from a list by the participant and/or intensity ratings provided for each emotion, text input, and/or answers to questions provided in the form of Likert scale ratings.

Figure 3:
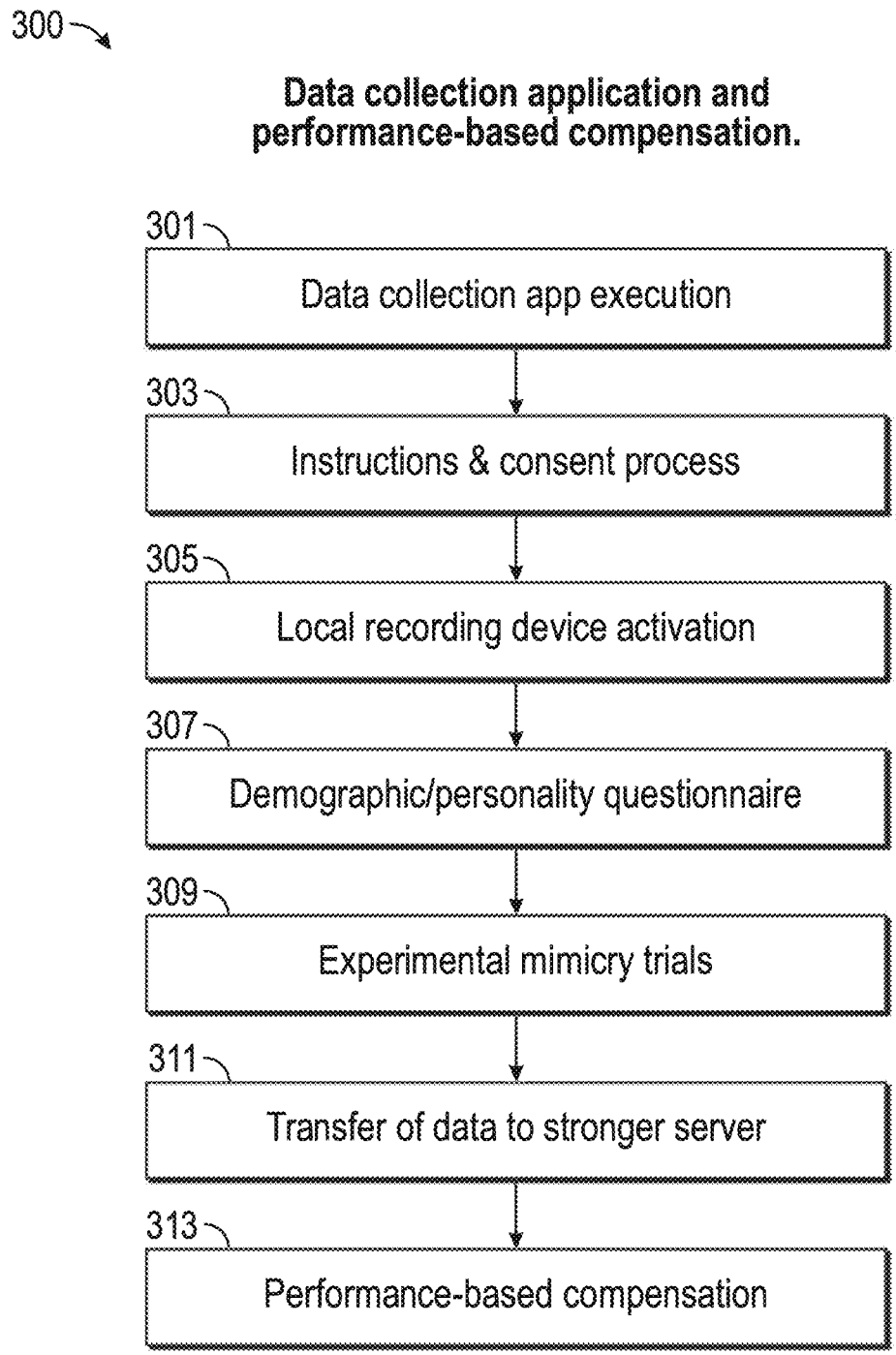
FIG. 3 illustrates an exemplary process for obtaining training data for machine-learning algorithms, in accordance with some embodiments of this disclosure.

FIG. 3 illustrates an exemplary process 300 for obtaining data training data to be used for training machine-learning algorithms according to embodiments of this disclosure. Process 300 is performed, for example, using one or more electronic devices implementing a software platform. In some examples, process 300 is performed using a client-server system, and the blocks of process 300 are divided up in any manner between the server and a client device. In other examples, the blocks of process 300 are divided up between the server and multiple client devices. In other examples, process 300 is performed using only a client device or only multiple client devices. In process 300, some blocks are, optionally, combined, the order of some blocks is, optionally, changed, and some blocks are, optionally, omitted. In some examples, additional steps may be performed in combination with the process 300. Accordingly, the operations as illustrated (and described in greater detail below) are exemplary by nature and, as such, should not be viewed as limiting.

At Block 301, the system can receive an indication from a participant to open an application corresponding to the data collection application used to obtain the training data from the participant. In one or more examples, the system can prompt the participant to download the application. Once the application is downloaded, the system can receive an indication from the participant to open the application. In one or more examples, the data collection application can be a website, a web application, a desktop application, or a mobile application.

At Block 303, the system can present instructions for completing the survey. In one or more examples, the system can prompt the participant to provide informed consent to participate. FIGS. 4A and 4B illustrate an exemplary consent form 400 provided to a user. In some embodiments, the system receives a completed consent form prior to receiving a recording from the participant.

In one or more examples, the system can further obtain consent from a participant regarding data to being collected using local recording devices, data transferred to a data storage server, and data shared with third parties and/or used to train empathic AI algorithms. FIG. 5 illustrates an exemplary audio release form 500 provided to a user. In some embodiments, the system receives a completed consent form prior to receiving a recording from the participant.

In some cases, the instructions explain that the participant will receive performance-based compensation in the form of bonuses that depend on a comparison between ratings or measures of participant recorded behaviors and ratings (e.g., measures) of the original stimulus.

At Block 305, the system can activate local recording devices, e.g., a webcam or microphone, of the participant's device. In one or more examples, the local recording device can be activated either immediately after consent is obtained or after the participant provides subsequent permission to activate the device by clicking on a designated button. In some examples, the system receives a "test" recording captured by the local device, which is validated automatically by the data collection application (based on file size, duration, and/or signal intensity) and/or upon inspection by the participant.

Figure 6:
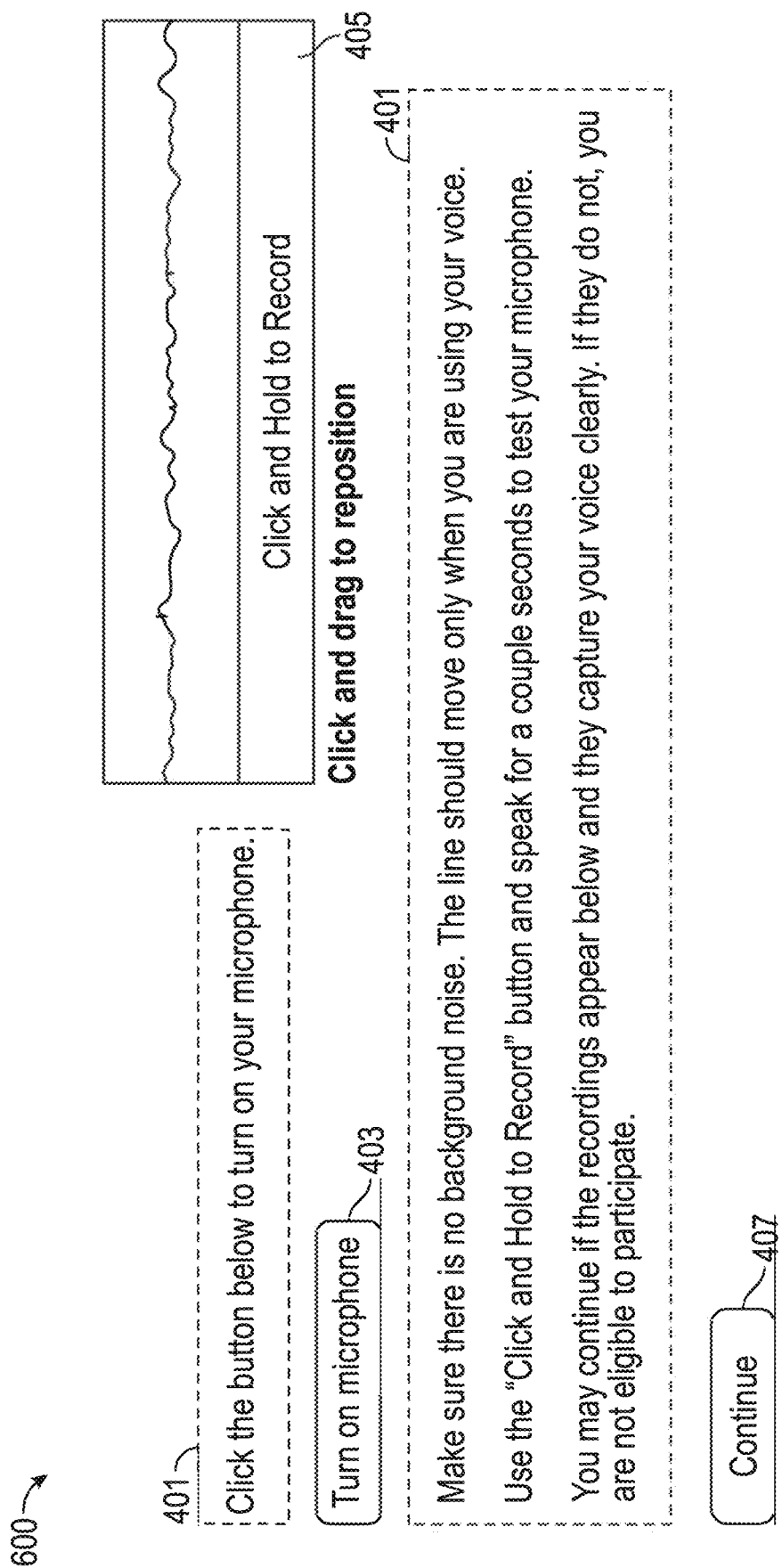
FIG. 6 illustrates an exemplary user interface, in accordance with some embodiments of this disclosure.

FIG. 6 illustrates an exemplary recording user interface 600 according to one or more embodiments of this disclosure. The exemplary recording user interface can be presented on a user device, e.g., a mobile device, tablet, laptop, etc. The exemplary recording user interface can include instructions 601, a microphone control 603, a recording user interface control 605, and a progression control 607. The microphone control 603 can be activated via a user input, e.g., click, to turn on the microphone of the mobile device. The recording user interface control 605 can be activated via a user input to capture a recording of the user via the microphone. In some examples, this UI can be used to capture a "test" recording by the user, for example, to ensure that the capture device is functioning properly. The progression control 607 can be activated via a user input to indicate that the user has completed a recording and/or advance to a subsequent UI. Although the figure is shown in relation to a microphone control, a skilled artisan will understand the user interface can include other capture devices, e.g., camera, that can be activated to capture a recording, according to embodiments of this disclosure. Further, this particular configuration of the UI is merely exemplary and other configurations can be implemented without departing from the scope of this disclosure.

At Block 307, the system can obtain answers to a demographic and personality questionnaire completed by the participant. In some embodiments, a participant can respond to a questionnaire collecting demographic and personality data, such as gender, age, race/ethnicity, country of origin, first and/or second language, and answers to psychological survey questions that indicate personality, well-being, mental health, and/or subjective socioeconomic status. This data may later be used to test for bias in trained machine-learning models, to calibrate trained machine-learning models in order to remove bias, and/or to incorporate methods of personalization into trained machine-learning models.

FIGS. 7A and 7B illustrate an exemplary demographic and personality questionnaire 700 according to one or more embodiments of this disclosure. As shown in the figure, the demographic and personality questionnaire can include one or more prompts and/or questions and a corresponding user-selection control. In some embodiments, the demographic and personality questionnaire can receive one or more selections, e.g., via the user-selection control, indicative of one or more characteristics of a user.

At Block 309, the system can present stimuli (e.g., an audio file, an image of a facial expression, etc.) and/or tasks (e.g., "imitate the facial expression", "act like a person who just won the lottery") to the participant in a pseudorandom order. The system can also prompt the participant to behave in a manner that depends on what they perceive in, or how they make sense of, the stimuli and/or tasks. As the participant responds to the stimuli and/or tasks, the system can activate local recording devices to record the participant's behavior. The stimuli and/or tasks may be selected to span dimensions of emotion identified in the psychology literature as well as newly hypothesized dimensions of emotion. For example, stimuli such as images, audio, and/or video have been used to evaluate emotions such as sexual desire, aesthetic appreciation, entrancement, disgust, amusement, fear, anxiety, interest, surprise, joy, horror, adoration, calmness, romance, awe, nostalgia, craving, empathetic pain, relief, awkwardness, excitement, sadness, boredom, triumph, admiration, satisfaction, sympathy, anger, confusion, disappointment, pride, envy, contempt, and guilt. For additional examples please refer to Cowen & Keltner, 2020, *Trends in Cognitive Sciences*, which is herein incorporated by reference.

In some embodiments, the system can present the participant with annotations of their recorded behaviors. In one or more examples a machine-learning model can be used to annotate the recorded behaviors. The system can also prompt the participant to generate behaviors that will meet a specific annotation criterion. For example, participants may be asked to behave such that the annotations include a specific emotion label (e.g., "produce a facial expression that is labeled surprise"), or participants may be asked to behave in such a way that the annotations produced by the machine-learning appear to be incorrect ("produce a facial expression that appears to be incorrectly labeled by the model").

FIG. 8 illustrates an exemplary mimicry user interface (UI) 800 according to one or more embodiments of this disclosure. In one or more examples, the mimicry UI 800 can be presented to a participant at Block 309. The exemplary mimicry UI 800 can include instructions 801, a playback control 803, a recording user interface control 805, and a plurality of predefined emotion tags 807. The playback control 803 can be activated via a user input, e.g., click, to play a media content, e.g., audio recording, video recording, image, etc. The recording user interface control 805 can be activated via a user input to capture a recording of the user via a microphone and/or camera of the user's device. The predefined emotion tags 807 can include a plurality of emotions that can be selected by a user and associated with the media content and/or recording as ratings. In one or more examples, the predefined emotion tags can include, but are not limited to, admiration, adoration, aesthetic appreciation, amusement, anger, annoyance, anxiety, approval, awe, awkwardness, boredom, calmness, compulsion, concentration, confusion, connectedness, contemplation, contempt, contentment, craving, curiosity, delusion, depression, determination, disappointment, disapproval, disgust, disorientation, distaste, distress, dizziness, doubt, dread, ecstasy, elation, embarrassment, empathetic pain, entrancement, envy, excitement, fear, frustration, gratitude, grief, guilt, happiness, hopelessness, horror, humor, interest, intimacy, irritability, joy, love, mania, melancholy, mystery, nostalgia, obsession, pain, panic, pride, realization, relief, romance, sadness, sarcasm, satisfaction, self-worth, serenity, seriousness, sexual desire, shame, spirituality, surprise (negative), surprise (positive), sympathy, tension, tiredness, trauma, triumph, warmth, and wonder. These emotion tags are exemplary, more or less emotion tags from this list may be included. In one or more examples, the emotion tags can further include synonyms and other grammatical forms of these emotion tags (e.g., adjectives such as "ashamed" instead of "shame" and "confused" instead of "confusion"). Accordingly, these exemplary emotion tags are not intended to limit the scope of the disclosure.

Although FIG. 8 is shown in relation to an audio content, a skilled artisan will understand the user interface can include other media content including, video content and one or more images, according to embodiments of this disclosure. Accordingly, the mimicry UI 800 can be provided to enable a participant to playback an experimental stimulus, record an imitation of the experimental stimulus and select one or more predefined emotion tags to characterize the experimental stimulus.

FIG. 9 illustrates an exemplary mimicry user interface (UI) 900 according to one or more embodiments of this disclosure. As discussed with respect to the FIG. 8, the exemplary mimicry UI can include instructions 901, a media content playback control 903, a recording user interface control 905, and a plurality of predefined emotion tags 907. As shown in mimicry UI 900, the UI can further include a recording playback control 909 and an emotion scale 911 corresponding to the selected emotions. The recording playback control 909 can be activated via a participant input to play a recording captured by the participant. For example, the system can receive an indication from the participant to playback the recording to determine if the recording is satisfactory. If the participant determines the recording is not satisfactory, the participant may capture a second recording using the recording user interface control 905. The emotion scale 911 can be provided for a participant to indicate a level of intensity of the emotion corresponding to the selected emotion tags associated with the media content.

FIG. 10 illustrates an exemplary mimicry user interface (UI) 1000 according to one or more embodiments of this disclosure. The exemplary mimicry UI 1000 can include instructions 1001, a media content 1003, a recording user interface control 1005, a recording 1009, and a plurality of predefined emotion tags 1007. The media content 1003 can be provided to the participant as a stimuli, whereby the participant attempts to imitate the media content 1003. The recording user interface control 1005 can be activated via a user input to capture a recording of the participant via a microphone and/or camera of the participant's device. In some embodiments, the recording user interface control 1005 can provide a preview of the data captured by a capture device. The recording 1009 can correspond to an image captured by the image capture device of the participant's device. As discussed above, the predefined emotion tags 1007 can include a plurality of emotions that can be selected by a user and associated with the media content and/or recording. Although exemplary mimicry UI 1000 is shown in relation to image content, a skilled artisan will understand the user interface is not limited to image capture and can include other media content including, audio and/or video.

FIG. 1100 illustrates exemplary feedback UI 1100 according to one or more embodiments of this disclosure. The exemplary feedback UI 1100 can be presented to a participant to collect participant feedback regarding the data collection process.

FIG. 1200 illustrates an exemplary user interface (UI) 1200 according to one or more embodiments of this disclosure. The exemplary user interface 1200 can be used to provide a completion code to a user for their personal records and for obtaining compensation.

At Block 311, the system can transfer the recorded data and survey data to a storage server. In one or more examples, the data can be transferred as participants undergo the experimental mimicry trials or upon completion of the survey.

At Block 313, the system can determine supplementary compensation based on a subsequent comparison between ratings or measures of participants' behavioral responses and ratings or measures of the original stimuli. Compensation can be provided to participants through a payment platform. For instance, a participant's recorded behavioral responses may be used as stimuli in surveys responded to by other participants. The other participants' responses may be used to determine the original participants' compensation.

As an example, the system can present a first set of stimuli to a first participant, receive a selection of a first set of emotion tags and corresponding emotion intensities associated with the first set of stimuli, and capture a first set of recordings by the first participant mimicking the first set of stimuli. The first set of recordings of the first participant may later be presented as a second set of stimuli to a second participant.

Accordingly, the system can present the second set of stimuli to the second participant and receive a selection of a second set of emotion tags and corresponding emotion intensities associated with the second set of stimuli. To the extent that the second set of emotion tags and intensities associated with the first recording/second stimulus are similar to the first set of emotion tags and intensities associated with the first stimulus, the participant can be rewarded a higher performance-based compensation. Measures of similarity for purpose of determining the performance-based compensation may include the percentage overlap in emotion tags, the correlation (such as the Pearson product-moment correlation coefficient) between emotion intensities associated the first recording and those associated with the first stimulus, or the inverse of the distance (such as Euclidean distance) between emotion intensities associated the first recording and those associated with the first stimulus.

In some embodiments, the system can determine the performance-based compensation based on a competition between multiple participants. For instance, the participant whose recordings are determined to be the most similar to the original stimuli may receive a reward. The performance-based compensation may also be informed by automated measures of a participant's responses by a machine-learning algorithm. For instance, participants who are presented with machine-learning-based annotations of their recorded behaviors during the experimental mimicry trials, and who are asked to behave in such a way that the annotations "appear to be incorrect", may be rewarded based on the degree to which the machine-learning-based annotations of their recorded behavioral response differ from other participants' ratings of their recorded behavioral response.

Figures 11, 12, 13A:
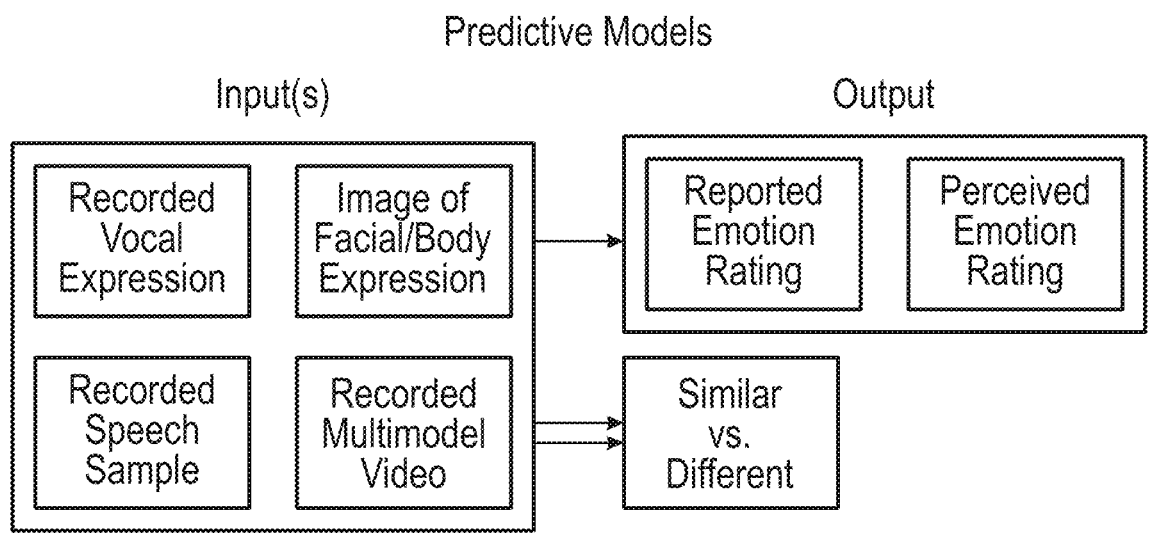
FIG. 11 illustrates an exemplary user interface, in accordance with some embodiments of this disclosure.
FIG. 12 illustrates an exemplary user interface, in accordance with some embodiments of this disclosure.
FIG. 13A illustrates an exemplary flowchart for predicting an emotional rating based on a stimulus input, in accordance with some embodiments of this disclosure.
Figure 13B:
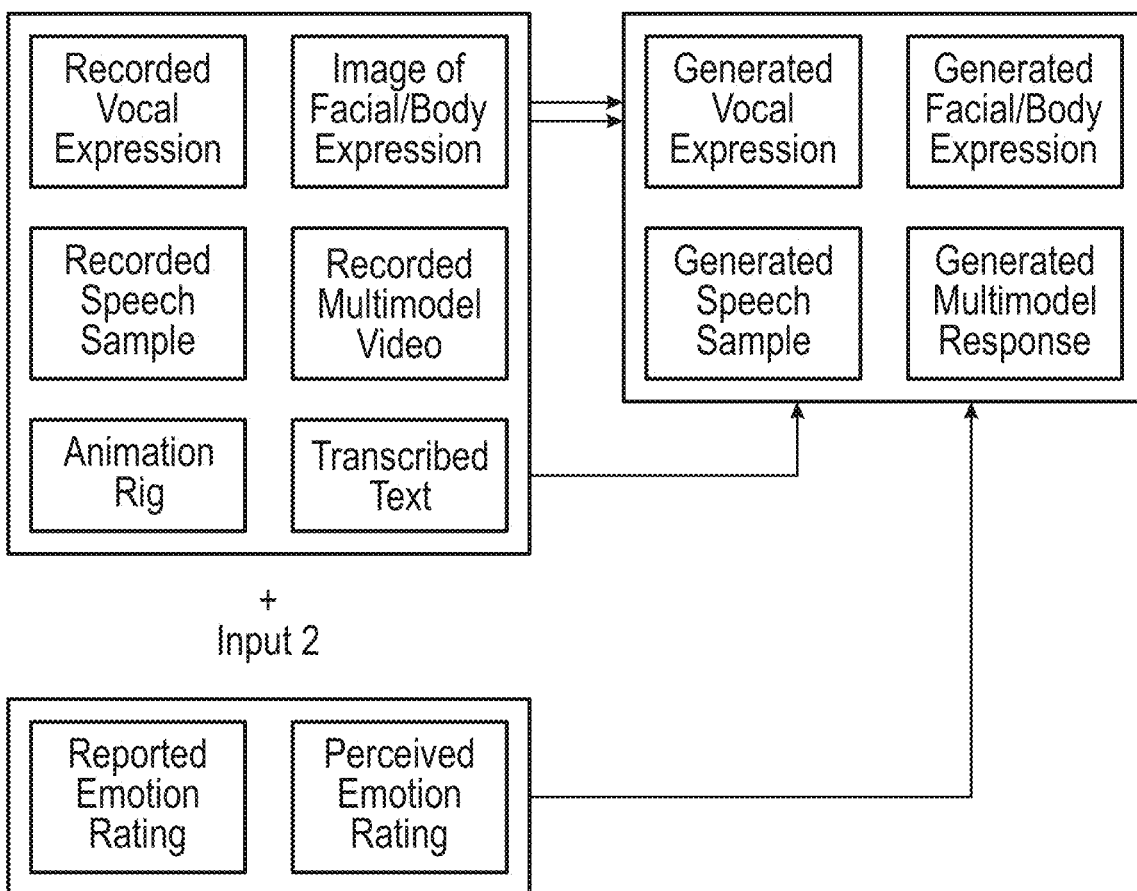
FIG. 13B illustrates an exemplary flowchart for generating an expression based on a stimulus input, in accordance with some embodiments of this disclosure.

FIGS. 13A and 13B illustrate an exemplary processes 1300A and 1300B for training machine-learning algorithms according to embodiments of this disclosure. Processes 1300A and 1300B are performed, for example, using one or more electronic devices implementing a software platform. In some examples, processes 1300A and 1300B are performed using a client-server system, and the blocks of processes 1300A and 1300B are divided up in any manner between the server and a client device. In other examples, the blocks of processes 1300A and 1300B are divided up between the server and multiple client devices. In other examples, processes 1300A and 1300B are performed using only a client device or only multiple client devices. In processes 1300A and 1300B, some blocks are, optionally, combined, the order of some blocks is, optionally, changed, and some blocks are, optionally, omitted. In some examples, additional steps may be performed in combination with the processes 1300A and 1300B. Accordingly, the operations as illustrated (and described in greater detail below) are exemplary by nature and, as such, should not be viewed as limiting.

FIG. 13A illustrates a process for predicting an emotional rating based on a stimulus input. As shown in the figure, the stimulus input can include one or more of a recorded vocal expression, an image of a facial and/or body expression, a recorded speech sample, or a recorded multimodal video. In one or more examples, these stimulus inputs can be input into a trained machine-learning model to predict a reported emotional rating or a perceived emotional rating. In one or more examples, the stimulus inputs can be input into a trained machine-learning model to predict similarities or differences between emotional experiences.

For example, in some embodiments, the data collected using the data collection application, e.g., data collection application 309, can be used to train empathic AI algorithms that predict participant emotion-related behavioral responses (ratings and recorded responses) from the properties of an experimental stimulus or task, from participants' other responses to the stimulus or task, or to make comparisons between different participants' responses to the same experimental stimulus or task.

In some embodiments, an algorithm is trained to predict emotion(s) based on image data (e.g., an image, a video) in which a person is producing a facial expression. The training data can comprise a plurality of images. Each training image can be a participant's imitation recording and is labeled with the participant's ratings of emotion. The predicted emotion (s) are consequently the emotions that the person would attribute to the expression they have produced. Other algorithms may be similarly trained to predict the emotions a person would attribute to their own speech, nonverbal vocalization (e.g., laugh or sigh), or the combination of facial, bodily, and/or vocal expressive behaviors captured in video.

Such empathic AI algorithms can provide an unbiased measure of user-generated emotional expressions that are useful for a wide range of downstream applications. For instance, such AI algorithms can be used in mental health diagnosis or treatment applications, wherein it is critical to obtain unbiased measures of the emotions a person experiences or conveys during a therapy session or in other contexts. For example, a therapy session and/or a medical appointment can be recorded. The recorded media can be provided to the empathic AI algorithm. Based on the recorded media, including one or more patient emotional expressions, the empathic AI algorithm may predict one or more emotions expressed by the patient during the therapy session and/or medical appointment. The predicted emotions can be used to supplement the physician's diagnosis and/or treatment.

Empathic AI algorithms that provide an unbiased measure of user-generated emotional expressions can also be used to build digital assistants that respond appropriately to the user queries provided through audio or video recording devices, wherein unbiased measures of emotional expression are critical to understanding the implicit meaning of the query and generating a satisfactory response. For example, a user may pose a spoken query to a digital assistant. The digital assistant may use an empathic AI algorithm to predict (infer) the user's intended or implicit emotional intonation from the nonverbal aspects (speech prosody) of the recorded query. By considering the user's inferred emotional intonation, the digital assistant may generate a more context-appropriate response than would be afforded by the lexical (language) content of the query alone. For instance, if the inferred emotional intonation is one of frustration, and the user's query follows from a previous response by the digital assistant, then the digital assistant may deduce that the previous response was unsatisfactory, and it may consequently generate a new response that strongly differs from the previous response.

Empathic AI algorithms that provide an unbiased measure of user-generated emotional expressions can also be used in augmented or virtual reality applications, wherein emotional expressions are transferred onto virtual characters or used to create emotionally responsive interfaces or environments. For example, a model can be trained to predict emotion(s) based on a recording of a user and the system can create/modify virtual characters, or aspects of an AR/VR environment, based on the predicted emotion(s).

In some embodiments, the data collected using the data collection application 309 can also be used to train algorithms that predict the emotions a perceiver would attribute to an emotional expression of another individual, rather than the emotions someone would attribute to their own expression. The training data can comprise a plurality of images. Each training image can be an image that is presented to a participant (e.g., the stimuli) and is labeled with the participant's ratings of emotion. In some embodiments, such algorithms can be implemented in application areas such as the development of digital assistants that produce facial or vocal expressions that are maximally understandable to a particular user. For example, a user may pose a query to a digital assistant. In response, the digital assistant may generate a response that includes one or more emotion-based expressions using an empathic AI algorithm that is trained to produce emotionally intoned speech from text (i.e., a generative model of emotional intoned speech). In order to enhance the user's understanding of the digital assistant's response, the generative model may incorporate background information on the user in order to predict the user's individual propensity to perceive specific emotions in various patterns of speech prosody. The response provided to the user may then be calibrated based upon these predictions. For instance, if the user expresses frustration in their query, the digital assistant may elect to respond using an emotional intonation that the user would be likely perceived as apologetic.

In some embodiments, in addition to predicting ratings or labels of emotional expressions, the data collected using the data collection application can also be used to train empathic AI algorithms that compute similarities or differences between emotional experiences in a manner that does not rely on ratings or labels. For instance, an algorithm can be trained to predict whether a given facial expression is an imitation of another facial expression (e.g., a classification, regression, or clustering/embedding model that receives a given facial expression and determines whether it is an imitation of a predefined facial expression), or whether two different facial expressions are imitations of the same facial expression (e.g., a classification, regression, or clustering/embedding model that receives two facial expressions and determine if they are imitations of the same expression).

In some embodiments, algorithms could identify subtle qualities emotional expressions that cannot easily be verbalized or extracted from human ratings. This may be preferable in application areas where it is important to account for relatively subtle and difficult to verbalize distinctions between expressions, such as in digital coaching for actors, wherein a user may be tasked with reproducing a targeted emotional expression. For example, a user may be provided with a prompt configured to solicit an expressive response from the user. For instance, the user may be asked to imitate a short video or audio clip presenting a subtle emotional expression. The user may provide an expressive response based on the prompt that can be fed into the empathic AI algorithm. The AI algorithm may be configured to receive the user's response and determine whether the user's response is an accurate imitation of the original emotional expression. The system can provide feedback to the user accordingly.

FIG. 13B illustrates a process for generating an emotional expression based on a stimulus input and an emotional rating. As shown in the figure the stimulus inputs can include one or more of a recorded vocal expression, an image of a facial and/or body expression, a recorded speech include one or more of sample, a recorded multimodal video, an animation rig, or transcribed text. Additional inputs can include an emotional rating input selected from one or more of a reported emotion rating and a perceived emotional rating. The stimulus input and the emotional rating inputs can be input into a machine-learning model to generate one or more outputs corresponding to a generated emotional expression. As shown in the figure, the generated emotional expression can include one or more of a generated vocal expression, a generated facial and/or body expression, a generated speech sample, and a generated multi-modal response.

In some embodiments, the data collected using the data collection application can also be used to train models that take emotion labels as input and generate facial or vocal expressions. This is useful, for example, in developing digital assistants that produce speech with contextually appropriate emotional intonations.

In some embodiments, the data collected using the data collection application can also be used to train semi-supervised models. As discussed above, the participant may be asked to provide a recording without providing emotion tags. Recordings collected based on the same stimulus can be used to train the semi-supervised model.

The machine-learning models described herein include any computer algorithms that improve automatically through experience and by the use of data. The machine-learning models can include supervised models, unsupervised models, semi-supervised models, self-supervised models, etc. Exemplary machine-learning models include but are not limited to: linear regression, logistic regression, decision tree, SVM, naive Bayes, neural networks, K-Means, random forest, dimensionality reduction algorithms, gradient boosting algorithms, etc.

In some embodiments, the demographic and personality data collected using the data collection application can be used to test for bias in trained machine-learning models, to calibrate trained machine-learning models in order to remove bias, and/or to incorporate methods of personalization into trained machine-learning models. For example, to test for bias in a trained machine-learning model, the model may be evaluated on data from participants of differing demographic groups to determine the differential effects of emotional expressions within each group on the predictions of the model. More specifically, a model trained to select images to surface to a user in an application (for instance, to preview a video or curate content within a social media feed) may be evaluated on data from participants of different genders. The differential effects of dominant expressions (e.g., anger, pride) and submissive expressions (e.g., embarrassment, gratitude) on the behavior of the model may then be examined within each gender group. One possible outcome, as an illustrative example, may be that the model is 25% more likely to surface images of female-presenting individuals with submissive expressions than with dominant expressions and 20% more likely to surface images of male-presenting individuals with dominant expressions than submissive expressions. Consequently, if the application is widely adopted, the model may reinforce harmful biases or stereotypes at a large scale, negatively affecting society. To remove this bias, the model may subsequently be calibrated to remove differences between gender groups in its relative treatment of dominant versus submissive expressions.

In some embodiments, models can be trained using supervised, semi-supervised, or unsupervised methods. As discussed above, when using supervised methods, participants' ratings are used as labels for the stimuli and/or participants' recorded behavioral responses. When using semi-supervised or unsupervised methods, links are drawn between stimuli and participants' responses, or among different participants' responses to the same stimuli, or among each participants' responses to different stimuli.

Examples

As discussed above, due to data limitations, empathic AI algorithms currently fail to recognize many dimensions of emotional expression and suffer from perceptual biases. For example, conventional AI systems for measuring emotional expressions are limited by the scope and generalizability of the training data. In images drawn from public sources, expressions such as the neutral face or posed smile are dramatically overrepresented, while expressions of genuine fear, anger, and many other emotions are very sparse. In datasets drawn from academia, the focus is generally on posed stereotypical facial expressions of six emotions (anger, disgust fear, happiness, sadness, and surprise), which represent only a tiny fraction of the emotional expressions found in everyday life. Consequently, machine-learning algorithms (e.g., empathic ML/AI algorithms) trained on these data do not generalize well to most real-life samples. Additionally, conventional AI systems for measuring emotional expressions are limited by perceptual biases in training data. Moreover, algorithms are biased by demographic imbalances in the expression of specific emotions within public sources of data. For example, academic datasets attempt to represent people of different demographics expressing the same emotions, but as noted above these datasets are generally very small and focus on a narrow range of emotional expressions.

By using methods and techniques described herein for collecting training data for empathic AI overcomes, these challenges can be overcome by using experimental manipulation to collect data that represents a richer, more balanced, and more diverse set of expressions, avoiding perceptual biases and confounds by gauging participants' own representations, beliefs, and/or ratings of the meanings of their expressions, and further avoiding perceptual biases and confounds by systematically collecting recordings of a balanced set of emotional expressions from different demographic or cultural groups.

As an example according to embodiments of this disclosure, a study was performed using large-scale controlled mimicry-based data to determine the meaning of various facial expressions for tens of thousands of people across six countries. This generated data suitable for both machine-learning and psychological inference. A deep neural network was configured to predict the culture-specific meanings people attributed to their own facial movements while disregarding physical appearance and context discovered 28 dimensions of facial expression with distinct meanings. Based on the collected data (e.g., facial expressions and attributed meanings), the study determined that the dimensions of facial expression were 63% preserved in meaning across the six countries and four languages, with 21 dimensions showing a high degree of universality and the remainder showing subtle to moderate cultural specificity. This is not an exhaustive catalog or taxonomy of distinct emotion concepts or anatomically distinct facial expressions. However, these findings indicate that the distinct meanings that facial expressions can reliably convey in a wide range of countries.

This study employed an experimental approach to address the limitations of previous large-scale studies of human facial expression. Perceptual ratings of naturally occurring facial expressions are generally confounded by the physical appearance and context of the person making the expression. Here, experimental randomization and mimicry were used to decouple facial movements from these confounds. In addition, while previous algorithms for measuring facial expression have been trained on ratings in a single culture using predetermined taxonomies of expression, and have captured a more limited range of facial expressions. The present study found a broader set of dimensions of facial movement that reliably mapped to culture-specific meanings, and used a deeply inductive approach to explore how these meanings converge and diverge across cultures.

Figure 14:
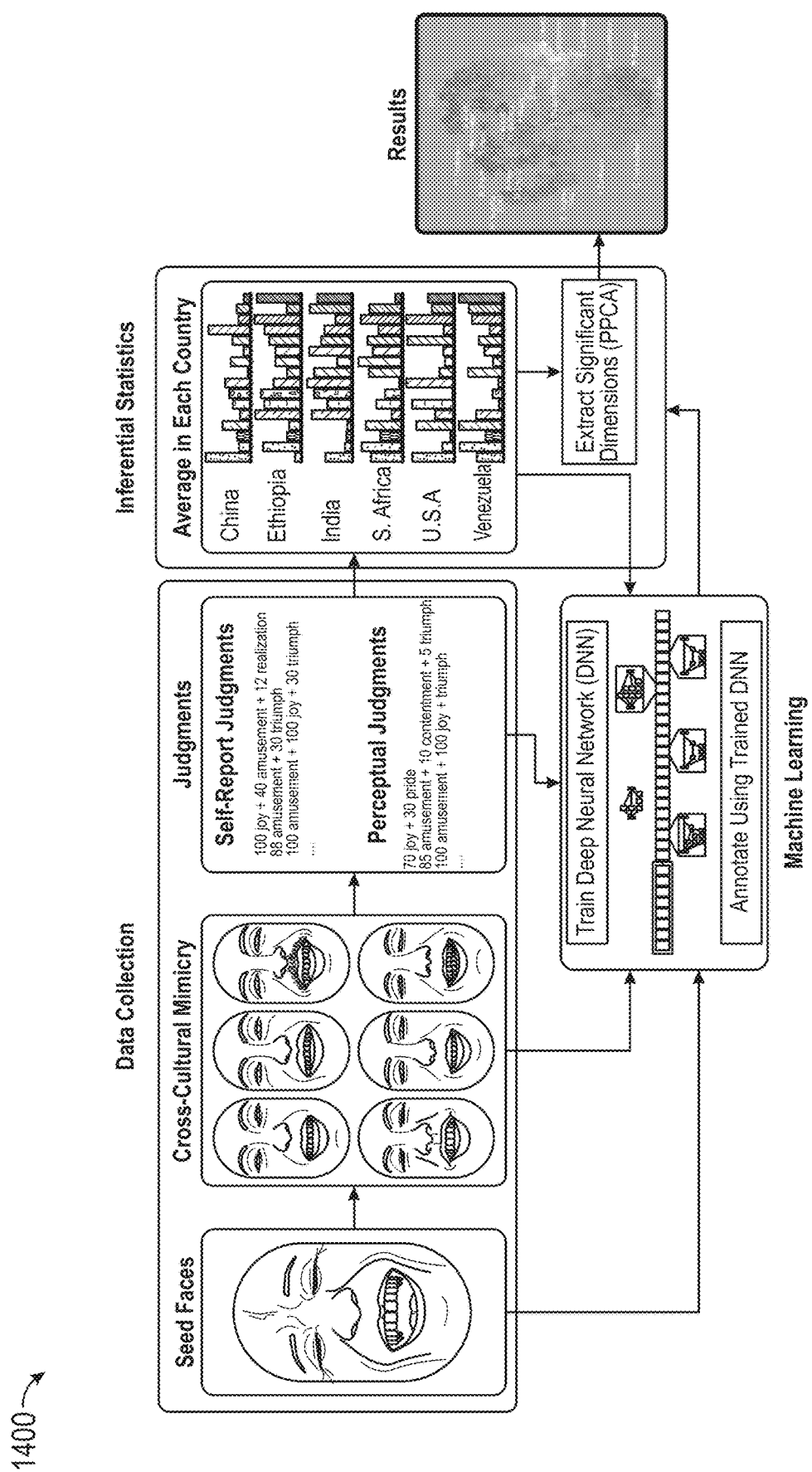
FIG. 14 illustrates an exemplary diagram for a process, in accordance with some embodiments of this disclosure.

FIG. 14 is a diagram that illustrates the process 1400 for this experimental study. In the first phase of data collection (henceforth "mimicry phase"), a total of 5,833 participants from China (n=602; 371 female), Ethiopia (n=149; 26 female), India (n=478, 74 female), South Africa (n=2,131; 970 female), the United States (n=2,576; 1,346 female), and Venezuela (n=344; 110 female) completed a facial expression mimicry task (e.g., cross-cultural mimicry task), imitating subsets of 4,659 images of facial expressions (e.g., seed images) and rating what each expression meant to them as they were imitating it (e.g., self-report judgments).

The six countries were selected due to being widely diverse in terms of culture-related values—e.g., individualism vs. collectivism, power distance, autonomy—of interest in cross-cultural comparisons. The seed images (e.g., experimental stimulus) included 4,659 images of individuals' facial expressions, extracted from naturalistic datasets of emotional stimuli, expressive behavior found online using hundreds of search queries for emotion concepts and emotional contexts, and responses to 1,707 emotionally evocative films. Based on past estimates of the reliability of observer judgments of facial expressions, the study collected responses to each seed image from an average of 15.2 separate participants in each culture. This amounted to a total of 423,193 experimental trials with associated mimic images and judgments on the meaning of the expression.

During the mimicry phase of data collection, study participants were instructed to participate in experimental mimicry trials as discussed above in processes 100 and 300. For example, prior to engaging in the mimicry task, participants were instructed to use their computer webcam to photograph themselves on each trial. During each trial, the system presented the participants with a user interface (e.g., user interfaces 1000) that presented the user with a target facial expression and instructed the participants to mimic the expression in the image such that their imitation would be rated similarly to the original image. This paradigm leverages the ability of most humans to mimic facial expressions (facial mimicry), which is observed early in development and often occurs spontaneously during social interaction.

On the same survey page, the system prompted participants to determine what they thought the person was feeling by selecting from forty-eight terms for emotions and rating each selection from 1-100, with values reflecting the perceived intensity of the emotion. Participants were prompted to select a value on a rating scale for at least one category. English terms were used in the three out of six countries where English is an official language (India, South Africa, and the United States). In China, ratings were collected in Chinese; in Ethiopia, ratings were collected in Amharic; and in Venezuela, ratings were collected in Spanish. This mimicry phase of data collection resulted in a large number of participant-generated "mimic" images in each culture [China (n=60,498), Ethiopia (n=29,773), India (n=58,054), South Africa (n=107,364), the United States (n=170,013), and Venezuela (n=47,734)] and self-report ratings corresponding to each mimic image that can simultaneously be considered perceptual ratings of each seed image. The mimic images are facial expression stimuli of high psychological validity: while posed, they have corresponding granular self-report judgments of the emotions the person in the image believes others will perceive.

Figure 15A:
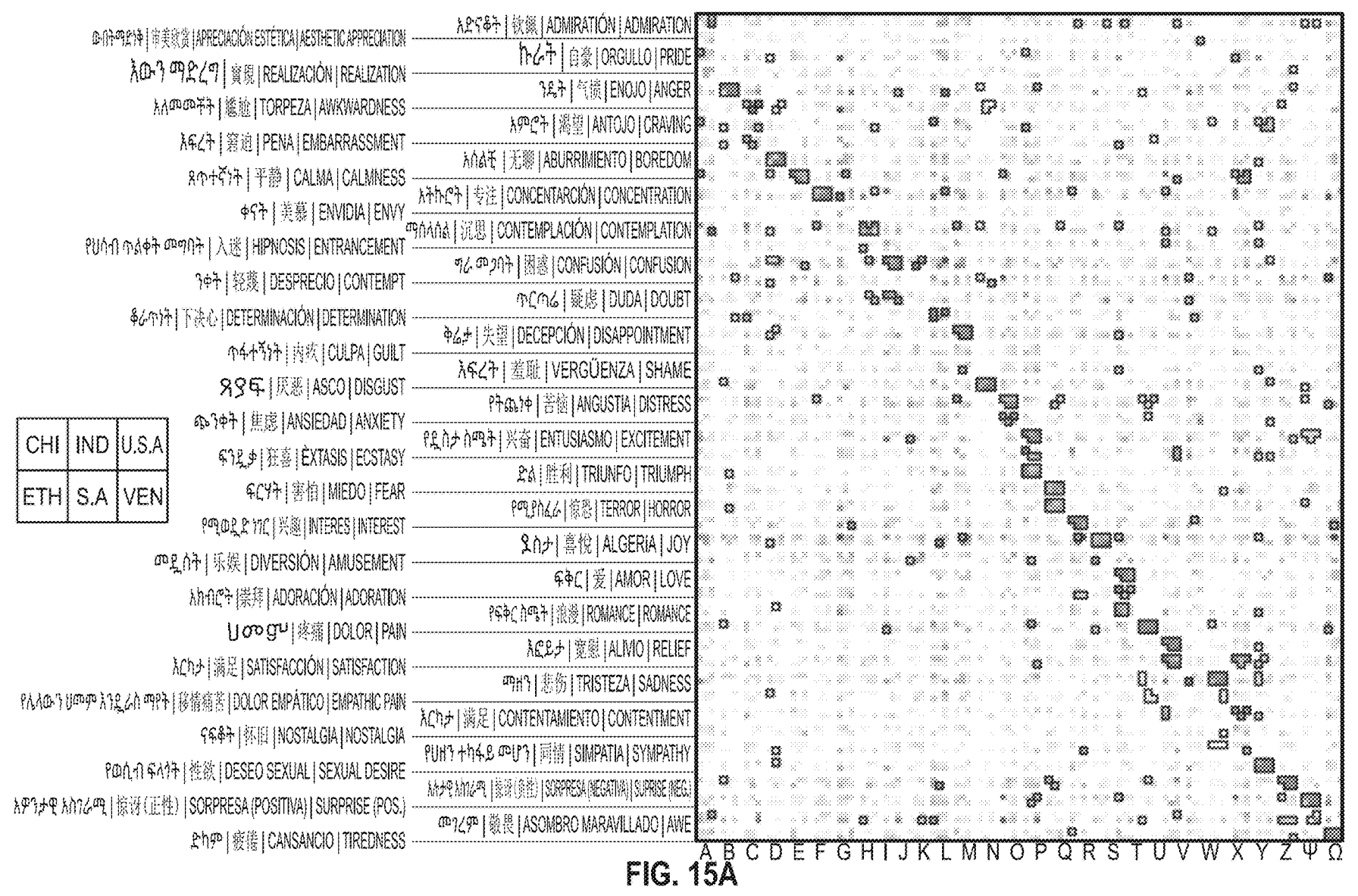

The study used these stimuli generated in the mimicry phase in the second phase of data collection (henceforth "perceptual judgment phase"), in which an independent set of participants from each culture [China (n=542; 349 female), Ethiopia (n=78; 18 female), India (n=1,101; 507 female), South Africa (n=2,465; 1,565 female), the United States (n=3,419; 1,983 female), and Venezuela (n=352; 118 female)] were recruited to complete an emotion perception task in which they rated mimic images from the first phase of data collection that were generated by participants within the same country. As in the mimicry phase of data collection, participants were asked to judge each face along 48 terms for emotions and provide intensity ratings ranging from 1-100. On average, participants in this phase of the experiment completed 77.1 trials. This amounted to a total of 534,459 judgments of all mimic images. FIG. 15A shows a distributions of emotion ratings for the mimic images from the perceptual judgment phase.

To identify the cross-cultural dimensions of perceived emotion using judgments of the seed images collected during the mimicry phase of data collection a generalized version (G-PPCA) of a principal preserved components analysis (PPCA) was applied to the collected data.

PPCA can be used to identify shared dimensions in the latent structure of two datasets measuring the same attributes. Like more established methods such as partial least-squares correlation analysis (PLSC) and canonical correlation analysis (CCA), PPCA examines the cross-covariance between datasets rather than the variance-covariance matrix within a single dataset. However, whereas PLSC and CCA derive two sets of latent variables, $\alpha$ and $\beta$, maximizing $Cov(X\alpha i, Y\beta i)$ or $Corr[X\alpha i, Y\beta i]$, PPCA derives only one variable: $\alpha$. The goal is to find dimensions of perceived emotion that reliably co-vary across both datasets X and Y.

Given the dataset measuring the same attributes comes from six different cultures in the study, a generalized version of the PPCA algorithm (G-PPCA) that extracts linear combinations of attributes that maximally co-vary across multiple datasets (in this case, emotion judgments from six countries) was developed. In particular, G-PPCA maximizes the objective function $Sum(Cov(\alpha^*X, \alpha^*Y)$ for X, Y in S) where S is the set of all possible pairwise combinations of datasets. The resulting components are ordered in terms of their level of positive covariance across all six datasets.

This G-PPCA was applied in a leave-one-stimulus-out manner to extract components from the judgments of all but one stimulus, and then projected each country's ratings of the left-out stimulus onto the extracted components, resulting in cross-validated component scores for each country and stimulus.

For example the G-PPCA was applied to judgments of the 4,659 seed images across the six countries. Based on this application, the system identified thirty-one semantic dimensions, or distinct kinds of emotion, preserved across all six cultures in emotion judgments of the seed images as shown in FIG. 15A. This extends prior work showing that perceivers reliably distinguish at least 28 dimensions of meaning in facial expression within a culture and that a high-dimensional semantic space organizes other components of emotional experience and perception across cultures. This work also converges with the high dimensional structure of emotion observed in more top down studies of emotion production and recognition.

However, despite the scale of the dataset, the findings from this first analysis could be explained in part by contextual influences on emotion perception such as visual context and demographic factors like gender and culture. In particular, the ratings that went into this analysis could be influenced by the subtle contexts visible in the periphery of each image as well as the demographic characteristics of the individuals forming expressions in the images, rather than just the information conveyed by the underlying facial movements.

To control for the effects of visual information beyond facial movement, the study trained a deep neural network (DNN) to predict the meanings attributed to facial movements while ignoring physical appearance and context, as discussed above. This permitted a structural taxonomy of expressive facial movement within and across cultures to be derived.

Referring to process 1400, the data collected from the mimicry phase and the perceptual judgment phase were input into a deep neural network (DNN). The DNN was configured to predict the average emotion judgments of each seed image in each culture from the images of participants mimicking each seed image. Because the seed images were each shown to a random set of participants, this method forced the DNN to ignore the physical appearance and context of the person making the expression (factors such as gender, age, clothing, and lighting that were randomized relative to the expression being imitated). The average emotion judgments within each culture (made in four separate languages) were treated as separate outputs. Thus, the DNN was not provided any prior mapping between emotion concepts and their use across countries or attempted translations across languages (English, Amharic, Chinese, and Spanish). The study used MTCNN to extract the faces from each mimic image, so only the face was used as input to the model.

After training, the study applied the DNN to the seed images (experimental stimulus to participants in the mimicry phase. The DNN was not exposed to these seed images during training. The study also applied a multidimensional reliability analysis method to distill the significant shared and culture-specific dimensions of facial expression uncovered by the DNN. For example, the study applied principal preserved components analysis (PPCA) between the DNN's culture-specific annotations of the seed images and the emotions actually inferred from the seed images by participants in each culture. Given that no prior was built into the model linking the words from different languages to one another, any relationship uncovered between the emotion concepts across languages using this method implies that the concepts were used similarly to describe the same facial movements.

For example, to identify dimensions of facial expression captured by the DNN that were reliably associated with distinct meanings in one or more cultures, we applied PPCA between the 288 outputs of the DNN applied to the seed images, which directly measure facial movement in the seed images, and the 288 averaged perceptual judgments of the seed images (ratings of 48 concepts in each of six countries). This analysis captures the dimensions along which country-specific perceptual judgments of naturalistic facial expressions are influenced by facial movement.

To assess the significance of the dimensions extracted using PPCA, the study used a leave-one-out cross-validation method. Specifically, the study iteratively performed PPCA between the DNN outputs and the averaged perceptual judgments of all but one of the seed images, and computed the scores of each dimension extracted by PPCA on the DNN outputs and averaged perceptual judgments of the held-out images. Finally, the study concatenated and correlated the PPCA scores of the held-out DNN outputs and judgments. To control for non-linear monotonic dependencies between extracted dimensions, the study used partial Spearman correlations, where for each PPCA dimension we controlled for the PPCA scores on all previous dimensions. To determine the significance of each dimension, the study used a bootstrapping method, iteratively repeating the correlation procedure while randomly resampling the seed images (1000 iterations with replacement). P-values were taken as one minus the proportion of times that the correlation exceeded zero across resampling iterations.

After computing p-values, we used a conservative method of correction for false discovery rate (FDR) that combined multiple FDR-correction methods. Specifically, the study used Benjamini-Hochberg FDR correction across the first 48 PPCA dimensions (as we were interested in variations of 48 potentially distinct emotion concepts and their translations across countries) at an alpha of 0.05. The study also separately performed a ForwardStop sequential FDR correction procedure. Finally, the study determined the signal-to-noise ratio (SNR) of the correlations corresponding to each PCA dimension (the correlation divided by the standard deviation computed using bootstrapping), and applied a threshold of 3 to the SNR to extract more stable dimensions. Dimensions that met all three of these criteria were retained. The study applied factor rotation using the varimax criterion to these dimensions.

To assess the significance of the individual loadings of emotion concepts on the extracted dimensions, the study used a bootstrapping method. Specifically, the study performed the entire PPCA analysis repeatedly after resampling the seed images with replacement, extracting the significant dimensions and performing factor analysis each time. For each dimension, the study then tested the significance of the top N loadings, with N varying from 1 to 288, by determining how often, across resampling iterations, there existed a dimension with all of these top N loadings pointing in the same direction. This estimates the proportion of times a dimension with these coloadings would be extracted if we repeated the entire study. The study took one minus this proportion as the p-value. As N varies from 1 to 288, the p-value can only increase because more loadings are included in the test (and therefore the probability of all loadings pointing in the same direction decreases monotonically). For each dimension, the study applied a ForwardStop FDR-correction procedure at an alpha of 0.05 to determine the number of significant loadings.

Using this method, (e.g., using both PPCA and DNN), the study identified twenty eight significant dimensions of facial expression that were reliably associated with distinct meanings, as shown in FIG. 15A. The study determined that each of the twenty eight dimensions corresponds to a pattern of facial movement that is reliably associated with a distinct set of emotion concepts in at least one country or language. Some facial expressions were found to have shared meanings across all six countries. For instance, the facial expressions corresponding to twelve different emotion concepts in English—"anger," "boredom," "concentration," "disgust," "fear," "joy," "pain," "sadness," "sexual desire," "surprise (positive)," "tiredness," and "triumph"—were categorized with what was previously determined were their most direct translations across all six countries and four languages. In four other cases, the correspondence was not exact, but very close: expressions that were associated with "contemplation" in some countries were associated with "doubt" in others, as was the case with "love" and "romance," "satisfaction" and "contentment," and "surprise (negative)" and the closest Amharic translation of "awe" (which is close in meaning to "surprise" in English). For another five dimensions— "calmness," "confusion," "disappointment," "distress," and "interest"—loadings were consistent in all six countries but not statistically significant in Ethiopia. Thus, a total of twenty one dimensions of facial expression showed a high degree of cultural universality in meaning across the 6 countries.

Figure 15B:
FIGS. 15B and 15C illustrate an exemplary visualization of the dimensions of facial expression, in accordance with some embodiments of this disclosure.
Figure 15C:

For some dimensions of facial expression, the study identified subtle cultural differences in meaning. FIGS. 15B and 15C illustrate the structural dimensions of facial expression that emerged as having distinct meanings within or across cultures. For example, the expression associated with "awkwardness" in three countries was associated with "determination" in Ethiopia and "craving" in Venezuela. The expression associated with "determination" in three countries was associated with "anger" and "joy" elsewhere. For example, a dimension associated with "calmness" and "satisfaction" in most countries ("Y" in FIGS. 15A-15C) was associated with "realization" in Ethiopia. There were stronger cultural differences in the meaning of the remaining four dimensions ("A," "G," "J," and "V").

The study found that twenty eight dimensions of facial expression—facial movements found to have reliable meanings in at least one country—were 63% preserved in both meaning and translation across the 6 countries ($r=0.80$, $r^2=0.63$, countrywise dimension loadings explained by the average loading), leaving the remaining 37% to be accounted for by either differences in meaning across cultures, imperfect translation across languages, and sampling error. This is shown in FIG. 16, which depicts loading correlations for each country and dimension (e.g., emotional meaning). Where there appeared to be cultural differences, the facial movements were nonetheless imitated very similarly across cultures, confirming that the findings from this study reflected differences in the meanings attributed to the underlying facial movements rather than in the ability to perceive or produce a given set of facial movements.

Figures 17A, 17B, 17C:
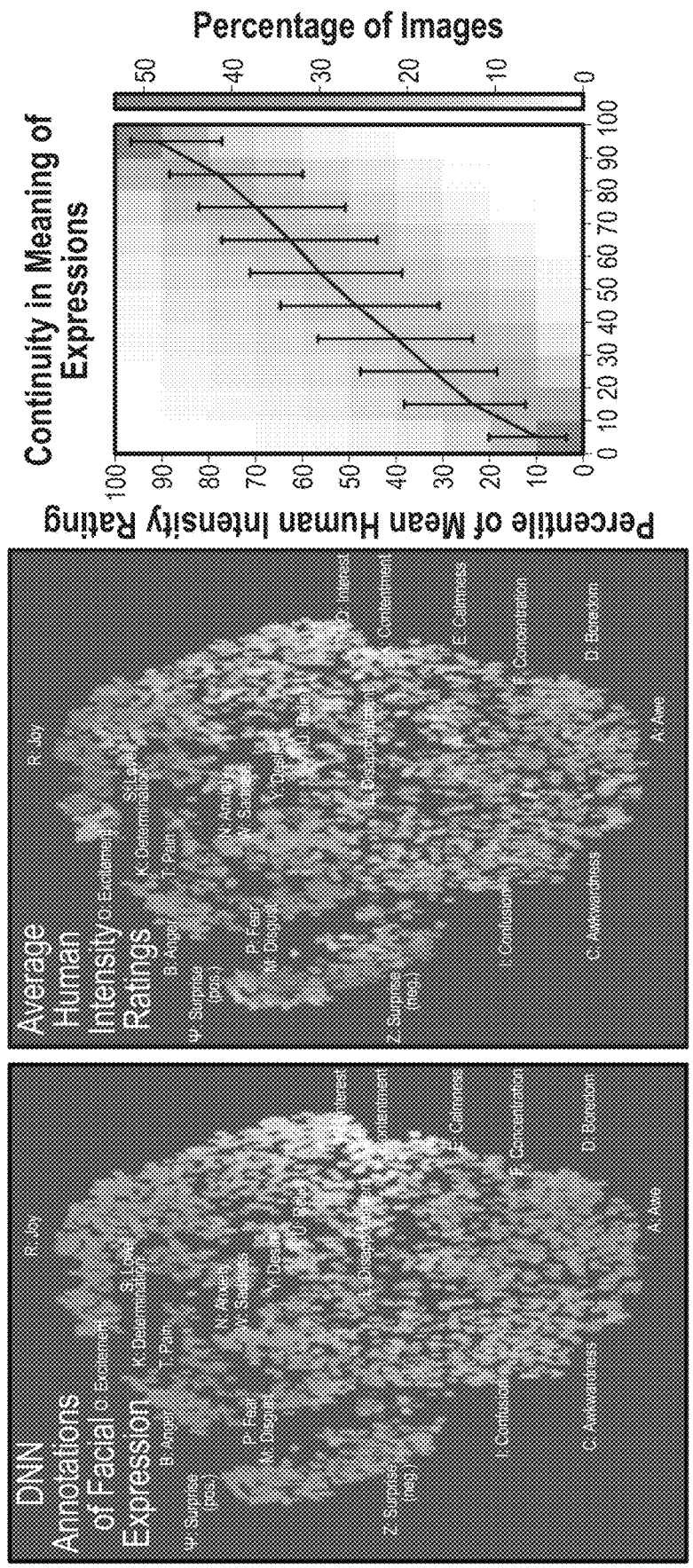
FIGS. 17A-17C illustrate the distribution of facial expressions along various dimensions found to have distinct meanings across cultures, in accordance with some embodiments of this disclosure.

Further, the study found that the emotions attributed to facial movements were not discrete in terms of clear boundaries between categories, but were heterogeneous and varied, reflecting continuous blends of meaning that were reliably associated with subtle combinations of facial movement. These results are reflected in FIGS. 17A-17C.

Figure 18:
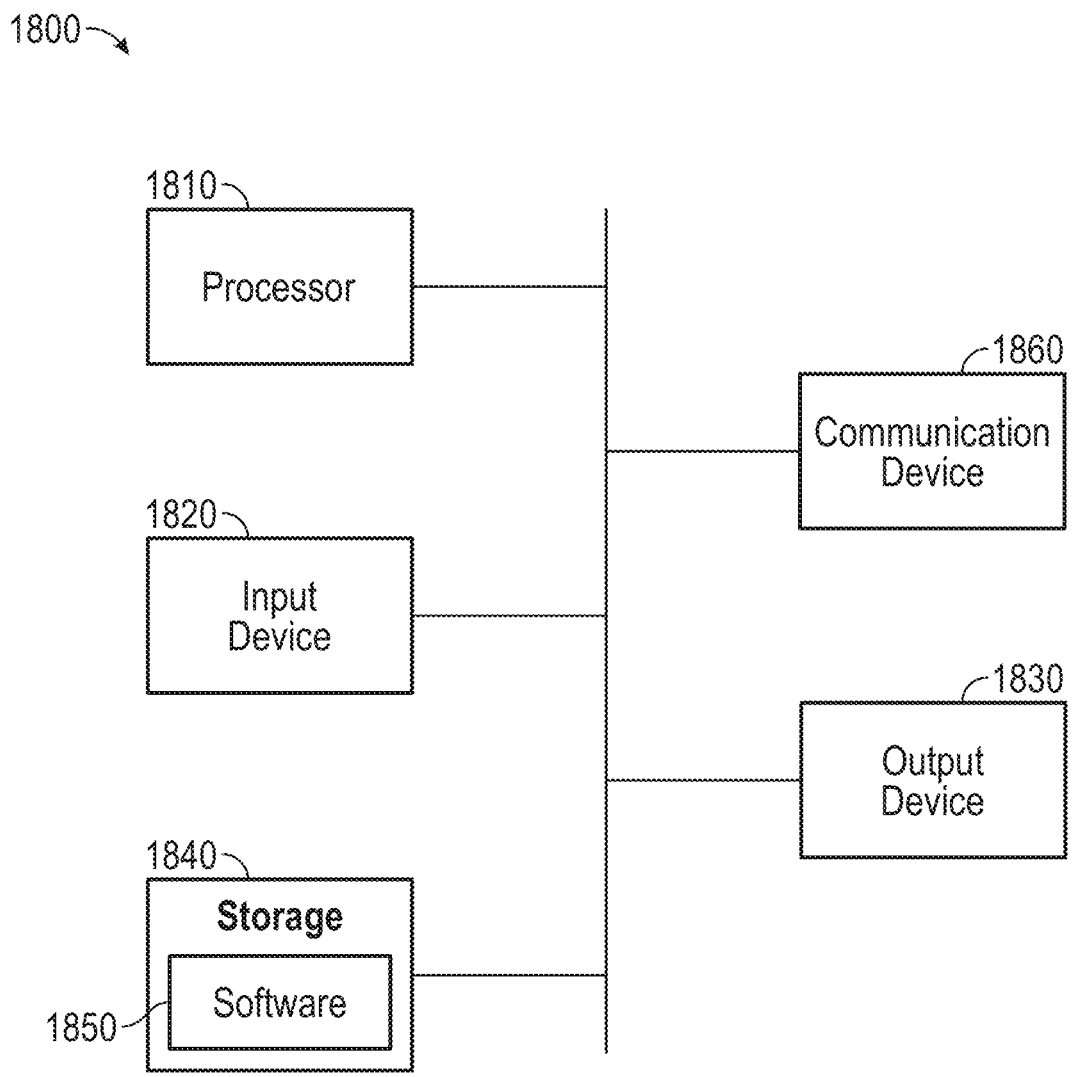
FIG. 18 illustrates an exemplary electronic device, in accordance with embodiments of this disclosure.

The operations described above with reference to the figures above are optionally implemented by components depicted in FIG. 18. It would be clear to a person having ordinary skill in the art how other processes are implemented based on the components depicted in FIG. 18.

FIG. 18 illustrates an example of a computing device in accordance with one embodiment. Device 1800 can be a host computer connected to a network. Device 1800 can be a client computer or a server. As shown in FIG. 18, device 1800 can be any suitable type of microprocessor-based device, such as a personal computer, workstation, server or handheld computing device (portable electronic device) such as a phone or tablet. The device can include, for example, one or more of processor 1810, input device 1820, output device 1830, storage 1840, and communication device 1860. Input device 1820 and output device 1830 can generally correspond to those described above, and can either be connectable or integrated with the computer.

Input device 1820 can be any suitable device that provides input, such as a touch screen, keyboard or keypad, mouse, or voice-recognition device. Output device 1830 can be any suitable device that provides output, such as a touch screen, haptics device, or speaker.

Storage 1840 can be any suitable device that provides storage, such as an electrical, magnetic or optical memory including a RAM, cache, hard drive, or removable storage disk. Communication device 1860 can include any suitable device capable of transmitting and receiving signals over a network, such as a network interface chip or device. The components of the computer can be connected in any suitable manner, such as via a physical bus or wirelessly.

Software 1850, which can be stored in storage 1840 and executed by processor 1810, can include, for example, the programming that embodies the functionality of the present disclosure (e.g., as embodied in the devices as described above).

Software 1850 can also be stored and/or transported within any non-transitory computer-readable storage medium for use by or in connection with an instruction execution system, apparatus, or device, such as those described above, that can fetch instructions associated with the software from the instruction execution system, apparatus, or device and execute the instructions. In the context of this disclosure, a computer-readable storage medium can be any medium, such as storage 1840, that can contain or store programming for use by or in connection with an instruction execution system, apparatus, or device.

Software 1850 can also be propagated within any transport medium for use by or in connection with an instruction execution system, apparatus, or device, such as those described above, that can fetch instructions associated with the software from the instruction execution system, apparatus, or device and execute the instructions. In the context of this disclosure, a transport medium can be any medium that can communicate, propagate or transport programming for use by or in connection with an instruction execution system, apparatus, or device. The transport readable medium can include, but is not limited to, an electronic, magnetic, optical, electromagnetic or infrared wired or wireless propagation medium.

Device 1800 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

Device 1800 can implement any operating system suitable for operating on the network. Software 1850 can be written in any suitable programming language, such as C, C++, Java or Python. In various embodiments, application software embodying the functionality of the present disclosure can be deployed in different configurations, such as in a client/server arrangement or through a Web browser as a Web-based application or Web service, for example.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims.

Exemplary Embodiments

Among the provided embodiments are:

1. A method for training a machine-learning model for predicting one or more emotions from received media data comprising:
   displaying a user interface comprising:
      a predefined media content,
      a plurality of predefined emotion tags, and
      a user interface control for controlling a recording of the user imitating the predefined media content;
   receiving, from a user, a selection of one or more emotion tags from the plurality of predefined emotion tags;
   receiving the recording of the user imitating the predefined media content;
   storing the recording in association with the selected one or more emotion tags;
   training, based on the recording, the machine-learning model configured to receive input media data and predict one or more emotions based on the input media data.

2. The method of embodiment 1, wherein displaying the user interface further comprises displaying a user interface control for providing a playback of the predefined media content.

3. The method of any of embodiments 1 to 2, further comprising displaying a preview of the recording on the user interface.

4. The method of embodiment 3, wherein the preview of the recording is displayed side-by-side with the predefined media content.

5. The method of any of embodiments 3 to 4, wherein the preview of the recording comprises a preview recording control for providing a playback of the recording.

6. The method of any of embodiments 1 to 5, further comprising:
   inputting data corresponding to a plurality of demographic groups into the trained machine-learning model to generate a plurality of outputs;
   identifying a bias of the trained machine-learning model based on the plurality of outputs.

7. The method of any of embodiments 1 to 6, further comprising:
   receiving one or more inputs indicative of one or more characteristics of the user;
   storing the recording in association with the one or more characteristics of the user;
   selecting the recording based on the associated one or more characteristics of the user; and
   training the machine-learning model based on the recording.

8. The method of embodiment 7, further comprising: displaying a prompt for the one user; and or more characteristics of the user.

9. The method of any of embodiments 7 to 8, wherein the one or more characteristics include one or more selected from a gender, an age, one or more races or ethnicities, a country of origin, a first language, a second language, personality, well-being, mental health, or a subjective socioeconomic status.

10. The method of any of embodiments 7 to 9, further comprising selecting the media content used to train the machine-learning model based on the one or more characteristics of the user.

11. The method of any of embodiments 1 to 10, wherein the predefined media content includes one or more of text data, audio, video, or image.

12. The method of any of embodiments 1 to 11, wherein the input media data includes one or more of text data, audio data, video data, or image data.

13. The method of any of embodiments 1 to 12, wherein the plurality of predefined emotion tags comprise one or more of admiration, adoration, aesthetic appreciation, amusement, anger, annoyance, anxiety, approval, awe, awkwardness, boredom, calmness, compulsion, concentration, confusion, connectedness, contemplation, contempt, contentment, craving, curiosity, delusion, depression, determination, disappointment, disapproval, disgust, disorientation, distaste, distress, dizziness, doubt, dread, ecstasy, elation, embarrassment, empathetic pain, entrancement, envy, excitement, fear, frustration, gratitude, grief, guilt, happiness, hopelessness, horror, humor, interest, intimacy, irritability, joy, love, mania, melancholy, mystery, nostalgia, obsession, pain, panic, pride, realization, relief, romance, sadness, sarcasm, satisfaction, self-worth, serenity, seriousness, sexual desire, shame, spirituality, surprise (negative), surprise (positive), sympathy, tension, tiredness, trauma, triumph, warmth, and wonder.

14. The method of any of embodiments 1 to 13, wherein the user is a first user, the method further comprising:
    receiving a second user's selection of one or more emotion tags from the plurality of emotion tags; and
    comparing the first user's selection and the second user's selection; and determining a compensation for the user.

15. The method of embodiment 14, further comprising: determining whether to train the machine-learning model using the recording based on the comparison.

16. The method of any of embodiments 14 to 15, further comprising receiving a second recording imitating the media content from the second user.

17. The method of any of embodiments 1 to 16, further comprising receiving a user input indicative of an intensity level corresponding to each of the selected emotion tags.

18. The method of any of embodiments 1 to 17, wherein the machine-learning model is one selected from a supervised model, an unsupervised model, and a self-supervised model.

19. A method for training a machine-learning model for generating a media output from an input indicative of an emotion comprising:
    providing a user interface comprising:
        a predefined media content,
        a plurality of predefined emotion tags, and
        a user interface control for controlling a recording of the user imitating the predefined media content;
    receiving, from a user, a selection of one or more emotion tags from the plurality of predefined emotion tags;
    receiving the recording of the user imitating the media content;
    storing the recording in association with the selected one or more emotion tags;
    training, based on the recording, the machine-learning model configured to receive an input indicative of an emotion and generate a media output comprising a vocal expression or a facial expression of the emotion.

20. The method of embodiment 19, wherein the media output is speech data.

21. The method of any of embodiments 19 to 20, wherein the media output is image data.

22. The method of any of embodiments 19 to 21, wherein displaying the user interface further comprises displaying a user interface control for providing a playback of the predefined media content.

23. The method of any of embodiments 19 to 22, further comprising displaying a preview of the recording on the user interface.

24. The method of embodiment 23, wherein the preview of the recording is displayed side-by-side with the predefined media content.

25. The method of any of embodiments 23 to 24, wherein the preview of the recording comprises a preview recording control for providing a playback of the recording.

26. The method of any of embodiments 19 to 25, further comprising:
    inputting data corresponding to a plurality of demographic groups into the trained machine-learning model to generate a plurality of outputs;
    identifying a bias of the trained machine-learning model based on the plurality of outputs.

27. The method of any of embodiments 19 to 26, further comprising:
    receiving one or more inputs indicative of one or more characteristics of the user;
    storing the recording in association with the one or more characteristics of the user;
    selecting the recording based on the associated one or more characteristics of the user; and
    training the machine-learning model based on the recording.

28. The method of embodiment 27, further comprising: displaying a prompt for the one or more characteristics of the user.

29. The method of any of embodiments 27 to 28, wherein the one or more characteristics include one or more selected from a gender, an age, one or more races or ethnicities, a country of origin, a first language, a second language, personality, well-being, mental health, or a subjective socioeconomic status.

30. The method of any of embodiments 27 to 29, further comprising selecting the media content used to train the machine-learning model based on the one or more characteristics of the user.

31. The method of any of embodiments 19 to 30, wherein the predefined media content includes one or more of text data, audio, video, or image.

32. The method of any of embodiments 19 to 31, wherein the input media data includes one or more of text data, audio data, video data, or image data.

33. The method of any of embodiments 19 to 32, wherein the plurality of predefined emotion tags comprise one or more of admiration, adoration, aesthetic appreciation, amusement, anger, annoyance, anxiety, approval, awe, awkwardness, boredom, calmness, compulsion, concentration, confusion, connectedness, contemplation, contempt, contentment, craving, curiosity, delusion, depression, determination, disappointment, disapproval, disgust, disorientation, distaste, distress, dizziness, doubt, dread, ecstasy, elation, embarrassment, empathetic pain, entrancement, envy, excitement, fear, frustration, gratitude, grief, guilt, happiness, hopelessness, horror, humor, interest, intimacy, irritability, joy, love, mania, melancholy, mystery, nostalgia, obsession, pain, panic, pride, realization, relief, romance, sadness, sarcasm, satisfaction, self-worth, serenity, seriousness, sexual desire, shame, spirituality, surprise (negative), surprise (positive), sympathy, tension, tiredness, trauma, triumph, warmth, and wonder.

34. The method of any of embodiments 19 to 33, wherein the user is a first user, the method further comprising:
receiving a second user's selection of one or more emotion tags from the plurality of emotion tags; and
comparing the first user's selection and the second user's selection; and determining a compensation for the user.

35. The method of embodiment 34, further comprising: determining whether to train the machine-learning model using the recording based on the comparison.

36. The method of any of embodiments 34 to 35, further comprising receiving a second recording imitating the media content from the second user.

37. The method of any of embodiments 19 to 36, further comprising receiving a user input indicative of an intensity level corresponding to each of the selected emotion tags.

38. The method of any of embodiments 19 to 37, wherein the machine-learning model is one selected from a supervised model, an unsupervised model, and a self-supervised model.

39. A user interface for training a machine-learning model for predicting one or more emotions of an input media data, comprising:
a predefined media content;
a plurality of predefined emotion tags; and
a user interface control for controlling a recording of the user imitating the predefined media content,
wherein the user interface is configured to:
receive, from a user, a selection of one or more emotion tags from the plurality of predefined emotion tags;
receive the recording of the user imitating the predefined media content; and
send the recording to the machine-learning model, and
wherein the recording is used to train the machine-learning model for predicting one or more emotions based on the input media data.

40. The user interface of embodiment 39, further comprising a control for providing a playback of the predefined media content.

41. The user interface of any of embodiments 39 to 40, further comprising a preview of the recording on the user interface.

42. The user interface of embodiment 41, wherein the preview of the recording is displayed side-by-side with the predefined media content.

43. The user interface of any of embodiments 41 to 42, wherein the preview of the recording comprises a preview recording control for providing a playback of the recording.

44. A method for predicting one or more emotions in a media data, comprising:
receiving the media data;
inputting the received media data into a trained machine-learning model, machine-learning model trained by a process comprising:
displaying a user interface comprising:
a predefined media content,
a plurality of predefined emotion tags, and
a user interface control for controlling a recording of the user imitating the predefined media content;
receiving, from a user, a selection of one or more emotion tags from the plurality of predefined emotion tags;
receiving the recording of the user imitating the predefined media content;
storing the recording in association with the selected one or more emotion tags;
training, based on the recording, the machine-learning model; and
predicting the one or more emotions in the received media data based on an output of the trained machine-learning model.

45. The method of embodiment 44, further comprising using the emotion prediction to create a diagnosis based on the emotion prediction.

46. The method of embodiment 44, further comprising interpreting a user utterance based on the emotion prediction.

47. The method of embodiment 44, further comprising generating an emotional expression on a virtual character in a virtual reality environment based on the emotion prediction.

48. The method of embodiment 44, further comprising altering a virtual reality environment based on the emotion prediction.

49. The method of embodiment 44, further comprising providing feedback of the media item based on the emotion prediction.

50. The method of embodiment 44, further comprising:
obtaining media content based on the emotion prediction; and
operating a virtual assistant based on the obtained media content.

51. The method of embodiment 44, further comprising:
obtaining media content based on the emotion prediction; and
modifying a virtual reality environment based on the media content.

52. A system for predicting one or more emotions in a media data, comprising:
one or more processors; and
a memory communicatively coupled to the one or more processors and configured to store instructions that, when executed by the one or more processors, cause the system to:
receive the media data;
input the received media data into a trained machine-learning model, the machine-learning model trained by a process comprising:
displaying a user interface comprising:
a predefined media content,
a plurality of predefined emotion tags, and
a user interface control for controlling a recording of the user imitating the predefined media content;
receiving, from a user, a selection of one or more emotion tags from the plurality of predefined emotion tags;
receiving the recording of the user imitating the predefined media content;
storing the recording in association with the selected one or more emotion tags;
training, based on the recording, the machine-learning model; and
predict the one or more emotions in the received media data based on an output of the trained machine-learning model.

53. The system of embodiment 52, wherein the instructions that, when executed by the one or more processors, further cause the system to use the emotion prediction to create a diagnosis based on the emotion prediction.

54. The system of any of embodiments 52 to 53, wherein the instructions that, when executed by the one or more processors, further cause the system to interpret a user utterance based on the emotion prediction.

55. The system of any of embodiments 52 to 54, wherein instructions that, when executed by the one or more processors, further cause the system to generate an emotional expression on a virtual character in a virtual reality environment based on the emotion prediction.

56. The system of any of embodiments 52 to 55, wherein instructions that, when executed by the one or more processors, further cause the system to alter a virtual reality environment based on the emotion prediction.

57. The system of any of embodiments 52 to 56, wherein instructions that, when executed by the one or more processors, further cause the system to provide feedback of the media item based on the emotion prediction.

58. The system of any of embodiments 52 to 57, wherein instructions that, when executed by the one or more processors, further cause the system to:
obtain media content based on the emotion prediction; and
operate a virtual assistant based on the obtained media content.

59. The system of any of embodiments 52 to 58, wherein instructions that, when executed by the one or more processors, further cause the system to:
obtain media content based on the emotion prediction; and
modify a virtual reality environment based on the media content.

The foregoing description, for purpose of explanation, has been described with reference to specific embodiments. However, the illustrative discussions above are not intended to be exhaustive or to limit the disclosure to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

The invention claimed is:

1. A method for generating media data, the method comprising:
displaying a predefined media content and a plurality of predefined expression tags;
receiving, from a user, a selection of one or more expression tags from the plurality of predefined expression tags;
receiving a recording of the user imitating the predefined media content;
training a machine learning model based on the recording of the user and the selected one or more expression tags; and
generating a media output by providing an input indicative of an expression to the trained machine learning model.

2. The method of claim 1, wherein the media output comprises at least one of a generated vocal expression, a generated facial expression, a generated body expression, a generated speech sample, or a generated multi-modal expression corresponding to the input.

3. The method of claim 1, wherein the media output comprises at least one of speech data and image data.

4. The method of claim 1, wherein the predefined media content and the plurality of predefined expression tags are displayed on a user interface comprising a user interface control.

5. The method of claim 4, comprising: displaying a preview of the recording on the user interface.

6. The method of claim 5, wherein the preview of the recording is displayed side-by-side with the predefined media content.

7. The method of claim 5, wherein the preview of the recording comprises a preview recording control for providing a playback of the recording.

8. The method of claim 1, comprising: inputting data corresponding to a plurality of demographic groups into the trained machine-learning model to generate a plurality of outputs; and identifying a bias of the trained machine-learning model based on the plurality of outputs.

9. The method of claim 1, wherein training the machine learning model comprises: associating the recording with one or more characteristics of the user; selecting the recording based on the associated one or more characteristics of the user; and training the machine-learning model based on the selected recording.

10. The method of claim 9, comprising: displaying a prompt for the one or more characteristics of the user.

11. The method of claim 9, wherein the one or more characteristics include one or more selected from a gender, an age, one or more races or ethnicities, a country of origin, a first language, a second language, personality, well-being, mental health, or a subjective socioeconomic status.

12. The method of claim 1, wherein the predefined media content includes one or more of text data, audio, video, or image.

13. The method of claim 1, wherein the input indicative of the expression comprises input media data and wherein the input media data includes one or more of text data, audio data, video data, or image data.

14. The method of claim 1, wherein the plurality of predefined emotion tags comprise one or more of admiration, adoration, aesthetic appreciation, amusement, anger, annoyance, anxiety, approval, awe, awkwardness, boredom, calmness, compulsion, concentration, confusion, connectedness, contemplation, contempt, contentment, craving, curiosity, delusion, depression, determination, disappointment, disapproval, disgust, disorientation, distaste, distress, dizziness, doubt, dread, ecstasy, elation, embarrassment, empathetic pain, entrancement, envy, excitement, fear, frustration, gratitude, grief, guilt, happiness, hopelessness, horror, humor, interest, intimacy, irritability, joy, love, mania, melancholy, mystery, nostalgia, obsession, pain, panic, pride, realization, relief, romance, sadness, sarcasm, satisfaction, self-worth, serenity, seriousness, sexual desire, shame, spirituality, surprise (negative), surprise (positive), sympathy, tension, tiredness, trauma, triumph, warmth, and wonder.

15. The method of claim 1, wherein the user is a first user, the and the method comprises: receiving a second user's selection of one or more emotion tags from the plurality of emotion tags; comparing the first user's selection and the second user's selection; and determining a compensation for the user.

16. The method of claim 15, comprising: determining whether to train the machine learning model using the recording based on the comparison.

17. The method of claim 1, comprising: receiving a second recording imitating the predefined media content from the second user.

18. The method of claim 1, comprising: receiving a user input indicative of an intensity level corresponding to each of the selected expression tags.

19. A system for generating media data, the system comprising one or more processors, and a memory communicatively coupled to the one or more processors and configured to store instructions that, when executed by the one or more processors, cause the system to:
  display a predefined media content and a plurality of predefined expression tags;
  receive, from a user, a selection of one or more expression tags from the plurality of predefined expression tags;
  receive a recording of the user imitating the predefined media content;
  train a machine learning model based on the recording of the user and the selected one or more expression tags; and
  generate a media output by providing an input indicative of an expression to the trained machine learning model.

20. A non-transitory computer-readable storage medium storing one or more programs, the one or more programs comprising instructions, which when executed by one or more processors of an electronic device having a display, cause the electronic device to:
  display a predefined media content and a plurality of predefined expression tags;
  receive, from a user, a selection of one or more expression tags from the plurality of predefined expression tags;
  receive a recording of the user imitating the predefined media content;
  train a machine learning model based on the recording of the user and the selected one or more expression tags; and
  generate a media output by providing an input indicative of an expression to the trained machine learning model.

* * * * *